United States Patent [19]
Clemmons et al.

[11] Patent Number: 5,973,115
[45] Date of Patent: Oct. 26, 1999

[54] METHOD FOR POTENTIATING AND INHIBITING INSULIN-LIKE GROWTH FACTOR ACTIVITY

[75] Inventors: David R. Clemmons, Chapel Hill; Walker H. Busby, Jr., Carrboro, both of N.C.; Michael T. Brewer, Boulder, Colo.; Stephen P. Eisenberg, Boulder, Colo.; Robert C. Thompson, Boulder, Colo.

[73] Assignees: Amgen Inc., Thousand Oaks, Calif.; University of North Carolina, Chapel Hill, N.C.

[21] Appl. No.: 08/475,824

[22] Filed: Jun. 7, 1995

Related U.S. Application Data

[62] Division of application No. 08/286,792, Aug. 5, 1994, which is a continuation of application No. 07/908,801, Jul. 7, 1992, abandoned, which is a continuation of application No. 07/686,281, Apr. 16, 1991, abandoned, which is a continuation of application No. 07/180,759, Apr. 12, 1988, abandoned, which is a continuation-in-part of application No. 07/050,102, May 15, 1987, abandoned.

[51] Int. Cl.$^6$ .................................................. C07K 14/435
[52] U.S. Cl. ......................... 530/350; 536/23.5; 530/380
[58] Field of Search .................... 530/350, 380; 536/23.5, 23.1

[56] References Cited

U.S. PATENT DOCUMENTS

| | | | |
|---|---|---|---|
| 4,394,443 | 7/1983 | Weissman et al. | 435/6 |
| 4,716,112 | 12/1987 | Panayotatos | 435/69.1 |

FOREIGN PATENT DOCUMENTS

| | | |
|---|---|---|
| 0 294 021 | 12/1988 | European Pat. Off. . |
| WO 88/07863 | 10/1988 | WIPO . |
| WO 89/08667 | 9/1989 | WIPO . |

OTHER PUBLICATIONS

Povoa et al., "The somatomedin–binding protein isolated from a human hepatoma cell line is identical to the human aminotic fluid somatomedin–binding protein", Biochem. Biophys. Res. Comm., vol. 128, No. 3, pp. 1071–1078, May 1985.

Clemmons et al., "Cultured fibroblast monolayers secrete a protein that alters the cellular binding of somatomedin–C/nsulinlike growth factor I", J. Clin. Invest., vol. 77, pp. 1548–1556, May 1986.

Drop., J. of Clinical Endocrinology and Metabolism, 59(5), 899–907 (1984).

D'Ercole, J. of Clinical Endocrinology and Metabolism, 61(4), 612–617 (1985).

Grizzard, J. of Clinical Endocrinology and Metabolism, 58(3), 535–543 (1984).

Robert S. Bar et al., "Production of IGF–Binding Proteins by Vascular Endothelial Cells," Biochemical And Biophysical Research Communications, vol. 148, No. 2, pp. 734–739 (1987).

Watson et al., "Recombinant DNA: A Short Course", W.H. Freeman and Company, New York, pp. 75–90 (1983).

Elgin et al., PNAS, USA, 84:3254–3258 (1987).

Baxter et al., BBRC, 147:403–415 (1987).

Baxter et al., BBRC, 139:1256–1261 (1986).

Mottola et al., J. Biol. Chem., 261:11180–11188 (1986).

Rutanen et al., J. Clinical Endocrinology and Metabolism, 66:173–180 (1988).

Lee et al., Molecular Endocrinology, 2:404–411 (1988).

Suggs et al., "Use of Synthetic Oligonucleotides as Hybridization Probes: Isolation of Cloned cDNA Sequences for Human $\beta_2$–microglobulin," Proc. Natl. Acad. Sci., USA, vol. 78, No. 11, (Nov. 1981), pp. 6613–6617.

Marston, "The Purification of Eukaryotic Polypeptides Synthesized in *Escherichia coli*," Biochem. J. 240, 1–12 (1986).

*Primary Examiner*—David Guzo
*Attorney, Agent, or Firm*—Finnegan, Henderson, Farabow, Garrett, & Dunner, L.L.P.

[57] ABSTRACT

Insulin-like growth factor I and II binding protein have potentiating and inhibiting activities. Cloning vectors and portable DNA sequences are disclosed.

2 Claims, 9 Drawing Sheets

```
          10         20         30         40         50         60
CCGCCGCCACCCTCCCAGAGAGCACTGGCCACCGCTCCACCATCACTTGCCCAGAGTTTG
          70         80         90        100        110        120
GGCCACCGCCCGCCGCCACCAGCCCAGAGAGCATCGGCCCCTGTCTGCTGCTCGCGCCTG
         130        140        150        160        170        180
GAGATGTCAGAGGTCCCCGTTGCTCGCGTCTGGCTGGTACTGCTCCTGCTGACTGTCCAG
    MetSerGluValProValAlaArgValTrpLeuValLeuLeuLeuThrValGln
         190        200        210        220        230        240
GTCGGCGTGACAGCCGGCGCTCCGTGGCAGTGCGCGCCCTGCTCCGCCGAGAAGCTCGCG
ValGlyValThrAlaGlyAlaProTrpGlnCysAlaProCysSerAlaGluLysLeuAla
         250        260        270        280        290        300
CTCTGCCCGCCGGTGTCCGCCTCGTGCTCGGAGGTCACCCGGTCCGCCGGCTGCGGCTGT
LeuCysProProValSerAlaSerCysSerGluValThrArgSerAlaGlyCysGlyCys
         310        320        330        340        350        360
TGCCCGATGTGCGCCCTGCCTCTGGGCGCCGCGTGCGCGGTGGCGACTGCACGCTGCGCC
CysProMetCysAlaLeuProLeuGlyAlaAlaCysAlaValAlaThrAlaArgCysAla
         370        380        390        400        410        420
CGGGGACTCAGTTGCCGCGCGCTGCCGGGGGAGCAGCAACCTCTGCACGCCCTCACCCGC
ArgGlyLeuSerCysArgAlaLeuProGlyGluGlnGlnProLeuHisAlaLeuThrArg
         430        440        450        460        470        480
GGCCAAGGCGCCTGCGTGCAGGAGTCTGACGCCTCCGCTCCCCATGCTGCAGAGGCAGGG
GlyGlnGlyAlaCysValGlnGluSerAspAlaSerAlaProHisAlaAlaGluAlaGly
         490        500        510        520        530        540
AGCCCTGAAAGCCCAGAGAGCACGGAGATAACTGAGGAGGAGCTCCTGGATAATTTCCAT
SerProGluSerProGluSerThrGluIleThrGluGluGluLeuLeuAspAsnPheHis
         550        560        570        580        590        600
CTGATGGCCCCTTCTGAAGAGGATCATTCCATCCTTTGGGACGCCATCAGTACCTATGAT
LeuMetAlaProSerGluGluAspHisSerIleLeuTrpAspAlaIleSerThrTyrAsp
         610        620        630        640        650        660
GGCTCGAAGGCTCTCCATGTCACCAACATCAAAAAATGGAAGGAGCCCTGCCGAATAGAA
GlySerLysAlaLeuHisValThrAsnIleLysLysTrpLysGluProCysArgIleGlu
         670        680        690        700        710        720
CTCTACAGAGTCGTAGAGAGTTTAGCCAAGGCACAGGAGACATCAGGAGAAGAAATTTCC
LeuTyrArgValValGluSerLeuAlaLysAlaGlnGluThrSerGlyGluGluIleSer
         730        740        750        760        770        780
AAATTTTACCTGCCAAACTGCAACAAGAATGGATTTTATCACAGCAGACAGTGTGAGACA
LysPheTyrLeuProAsnCysAsnLysAsnGlyPheTyrHisSerArgGlnCysGluThr
         790        800        810        820        830        840
TCCATGGATGGAGAGGCGGGACTCTGCTGGTGCGTCTACCCTTGGAATGGGAAGAGGATC
SerMetAspGlyGluAlaGlyLeuCysTrpCysValTyrProTrpAsnGlyLysArgIle
         850        860        870        880        890        900
CCTGGGTCTCCAGAGATCAGGGGAGACCCCAACTGCCAGATATATTTTAATGTACAAAAC
ProGlySerProGluIleArgGlyAspProAsnCysGlnIleTyrPheAsnValGlnAsn
```

*FIG. 6A*

```
         910       920       930       940       950       960
TGAAACCAGATGAAATAATGTTCTGTCACGTGAAATATTTAAGTATATAGTATATTTATA
End
         970       980       990      1000      1010      1020
CTCTAGAACATGCACATTTATATATATGTATATGTATATATATAGTAACTACTTTT
        1030      1040      1050      1060      1070      1080
TATACTCCATACATAACTTGATATAGAAAGCTGTTTATTTATTCACTGTAAGTTTATTTT
        1090      1100      1110      1120      1130      1140
TTCTACACAGTAAAAACTTGTACTATGTTAATAACTTGTCCTATGTCAATTTGTATATCA
        1150      1160      1170      1180      1190      1200
TGAAACACTTCTCATCATATTGTATGTAAGTAATTGCATTTCTGCTCTTCCAAAGCTCCT
        1210      1220      1230      1240      1250      1260
GCGTCTGTTTTAAAGAGCATGGAAAAAACTTGCCTAGAAAATGAAAATGAAATAAGAGAG
        1270      1280      1290      1300      1310      1320
AGTAGTTTTTCAGCTAGTTTGAAGGAGGACGGTTAACTTGTATATTCCACCATTACATTT
        1330      1340      1350      1360      1370      1380
GATGTACATGTGTAGGGAAAGTTAAAAGTGTTGATTACATAATAAAGCTACCTGTGGTGA
        1390      1400      1410      1420      1430      1440
TGTTGCCACCTGTTAAAATGTACACTGGATATGTTGTTAAACACGTGTCTATAATGGAAA
        1450      1460      1470      1480
CATTTACAATAAATATTCTCGATGGAAAAAAAAAAAAAAA
```

FIG. 6B

METHOD FOR POTENTIATING AND INHIBITING INSULIN-LIKE GROWTH FACTOR ACTIVITY

This is a division of application Ser. No. 08/286,792, filed Aug. 5, 1994, which is a continuation of application Ser. No. 07/908,801 filed Jul. 7, 1992, now abandoned, which is a continuation of application Ser. No. 07/686,281 filed Apr. 16, 1991, now abandoned, which is a continuation of application Ser. No. 07/180,759 filed Apr. 12, 1988, now abandoned, which is a continuation-in-part of application Ser. No. 07/050,102, filed May 15, 1997, now abandoned.

This invention was made with government support under 1 R01 AG02331 awarded by the National Institutes of Health. The government has certain rights in the invention.

BACKGROUND OF THE INVENTION

This invention relates to methods for potentiating the activity of insulin-like growth factor. This invention also relates to a human insulin-like growth factors I and II (IGF-I and II) binding protein (stimulatory form) which has this activity and to methods for producing this binding protein. The binding protein (stimulatory form) has utility in potentiating follicular development in vivo and in vitro, potentiating wound and burn healing, ulcer healing, and for re-epithelialization of damaged tissue of the kidney, lung or skin. The protein may also have utility in potentiating healing of damaged neurons and oligodendrocytes.

In addition, this invention relates to a human insulin-like growth factor binding protein (inhibitory form). The IGF binding protein (inhibitory form) may be used to inhibit tumor growth, inhibit the progression or growth of atherosclerotic plaques, inhibit diabetic retinopathy, and inhibit pulmonary fibrosis.

Human insulin-like growth factor i (IGF-I), also termed somatomedin-C, is a growth hormone dependent growth factor that circulates in blood and is synthesized in many tissues. Growth factor IGF-I is useful as an additive to cell culture media to facilitate in vitro cell growth. Like other growth factors that circulate in plasma, such as EGF, the insulin-like growth factors are bound to a binding protein that forms a carrier protein-IGF-I complex and is believed to serve a transport function. Partially purified forms of this binding protein previously have been shown to inhibit the insulin-like actions of IGF-I. An acid stable binding subunit of this complex has been purified from blood, and its secretion can be stimulated by growth hormone.

Human insulin-like growth factor II is weakly or not at all growth hormone dependent and is synthesized in many tissues. Like IGF-I, it circulates bound to a binding protein that is believed to serve a transport function.

In contrast to the above growth factor binding proteins, extracellular fluids such as spinal, lymph, and amniotic fluids, and tissue extracts of brain, placenta, and pituitary contain forms of IGF binding protein that have different molecular weights and are not growth hormone dependent. They bind both IGF-I and IGF-II with affinities in the $10^{10}$ to $10^9$ $M^{-1}$ range. An IGF binding protein has also been shown to be secreted by some cell types in culture including human fibroblasts and MDA-231 cells. Impure preparations of the protein from amniotic fluid and a similar protein that is secreted by rat liver cells, have been shown to inhibit the effects of IGF-I and IGF-II on fibroblast DNA synthesis and on sulfate incorporation into cartilage.

However, all of the prior human proteins were actually mixtures of more than one protein. For the first time, the present inventors have developed a method to separate these binding proteins. It has been found that the protein mixture from amniotic fluid actually contained at least two protein constituents. These protein constituents were found to have greatly different activity, one being capable of stimulating or enhancing the activity of IGF-I and IGF-II and one capable of inhibiting the growth factor activity of IGF-I and IGF-II. These two constitutent proteins, whose isolation to substantial purity is described herein for the first time, are referred to for the purposes of this application as IGF binding protein (stimulatory form) and IGF binding protein (inhibitory form), respectively. Experiments have indicated that the proteins may differ in the type of post-translational modifications, possibly disulfide bond arrangements. Such changes may lead to differences in degree of aggregation that may account for the observed differences in cell or matrix binding of the IGFBP and its biological activity.

In addition to the above amniotic fluid IGF binding proteins, an IGF binding protein has been isolated by the present inventors from human fibroblast conditioned media. This form of IGF binding protein potentiates the action of IGF like the stimulatory form from amniotic fluid. It cross-reacts with polyclonal antibodies to the IGF (stimulatory form) but may not be the same protein.

The purified IGF binding proteins (stimulatory form) have an estimated molecular weight between 32–38K daltons. These purified proteins, when adherent to cell surfaces, cause an increase in the amount of IGF that binds to the IGF receptor and to cell surfaces. Surprisingly, this increased amount of bound IGF results in a synergistic potentiation of the IGF activity.

The substantially purified IGF binding protein (inhibitory form) also has a molecular weight of 32–38 KD but does not adhere to cell surfaces and elutes later on DEAE-cellulose columns.

In the discussion which follows, reference to IGF-I binding protein or to IGF-II binding protein should be considered to refer to either or both species, unless the context indicates otherwise. Also, the abbreviation IGFBP may be used to refer to an IGF binding protein.

SUMMARY OF THE INVENTION

It is an object of the present invention to provide compounds capable of increasing the activity of certain growth factors. In particular, it is an object of the present invention to provide compounds capable of increasing the activity of insulin-like growth factor types I and II (IGF-I and IGF-II).

It is also an object of the present invention to provide compounds capable of preventing the action of IGF-I and IGF-II.

It is an additional object of the present invention to provide methods for obtaining each of these proteins in substantially purified form. The methods which are provided for the purification of these compounds allow the compounds to retain their relative IGF-affecting activity. The methods are to include both methods for purifying the naturally-occurring proteins and recombinant-DNA methods for producing IGFBP in other cells, or in cultured cells, and for purifying these proteins.

To accomplish these objects and in accordance with the purposes of the present invention, a method for potentiating the cell growth effects of IGF is provided. This method comprises:

(a) Obtaining IGF binding protein (stimulatory form) in a substantially purified form; and (b) Exposing the cells whose growth is to be stimulated to the IGF binding protein (stimulatory form) and to IGF.

To also accomplish the objects and also in accordance with the purposes of the present invention, a method of reducing the cell growth effect of IGF is provided. This method comprises:

(a) Obtaining IGF binding protein (inhibitory form) in a substantially purified form; and (b) Exposing the cells whose growth is to be inhibited to the IGF binding protein (inhibitory form).

To further accomplish the objects of the present invention and in further accord with the purposes thereof, methods for purifying the IGF binding proteins (stimulatory form) and (inhibitory form) are provided. These methods provide both forms of IGF binding protein in a substantially purified state which retains its IGF affecting activity.

Additionally, to accomplish the methods of the present invention, the DNA sequence of an IGFBP cDNA is provided. This sequence enables the development of cloning systems for the recombinant-DNA means for production of IGFBP. In particular, methods and plasmids for producing and purifying IGFBP from *E. coli* are provided.

It is understood that both the foregoing general description and the following detailed description are exemplary and explanatory only and are not restrictive of the invention, as claimed. The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 6 is the amino acid and nucleotide sequence of IGFBP with a 24 amino acid signal sequence.

DETAILED DESCRIPTION OF THE PREFERRED EMBODIMENTS

Figure 1:
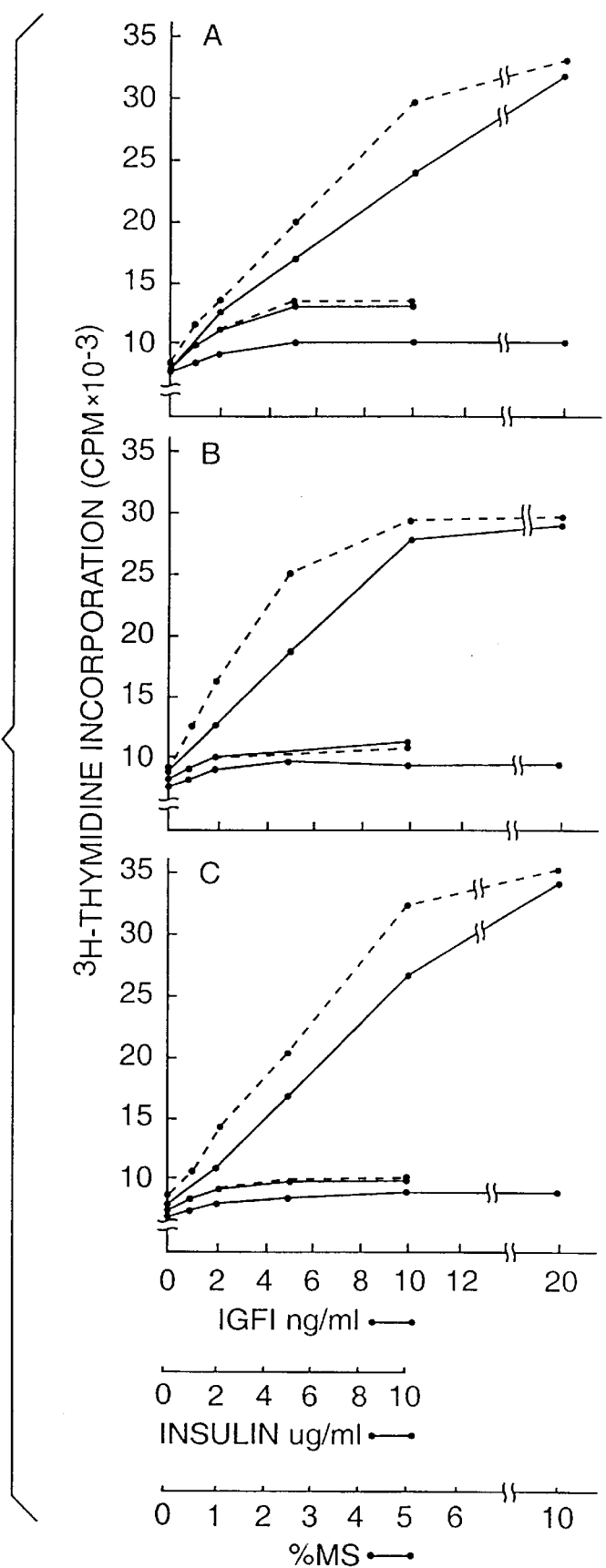
FIG. 1 (Parts A–C) depicts potentiation of DNA systhesis in porcine aortic smooth muscle cells (A) chick (B) mouse (C) embryo fibroblasts by IGF-I and binding protein. Smooth muscle cells were subcultured on microtest 96-well plates plating at 8,000 cells/well and allowing 5 days of the cells to become quiescent. Prior to the analysis, the cultures were washed two times with serum free DMEM followed by addition of the test substances in 0.2 ml DMEM supplemented with 0.5 uCi $_3$H-thymidine 1% human platelet poor plama (PPP). Chick embryo fibroblasts (2nd passage) were subcultured on 96-well microtest plates (Falcon 3004) 3,000 cells/well in DMEM supplemented with 10% FBS. Five days after plating the quiescent monolayers were exposed to the test factors listed plus 0.5 uCi/ml $^3$H-thymidine and 1% PPP. Mouse embryo fibroblast cultures between the 3rd and 5th passages were used and the experiments were performed as described for chick embryo fibroblasts except that the cells were plated at 8,000 cells/well. All cultures were exposed to increasing concentrations of human serum, insulin, IGF-I, IGF-I plus IGF-I binding protein (stimulatory form) (100 ng/ml), or insulin and IGF-I binding protein (stimulatory form), for 36 hours and $^3$H-thymidine incorporation was quantitated. The results are expressed as the mean of triplicate cultures.

Reference will now be made in detail to the presently preferred embodiments of this invention, which, together with the drawings and the following examples, serve to explain the principles of the invention.

As noted above, the present invention relates in part to a method for potentiating the effect on cells of insulin-like growth factors (IGF). It is known that IGF functions as growth factors by increasing the rate of DNA synthesis. The present inventors have obtained, in a substantially purified form, a protein which potentiates the growth promoting effects of IGF-I. This protein has been named IGF binding protein (stimulatory form). The potentiating effect of IGF binding protein (stimulatory form) on the ability of IGF-I to promote cell growth is depicted in FIGS. 1 through 4.

To obtain this potentiating effect, the IGF binding protein (stimulatory form) is obtained in a substantially purified form. In one embodiment, this substantially purifed IGF binding protein (stimulatory form) is first adhered to the surfaces of the target cells. increased. The target cells with the adhered IGF binding protein (stimulatory form) are then exposed to IGF-I. The exposure to IGF-I, coupled with the presence of the adhered IGF binding protein, results in at least about a four-fold increase in cellular growth rate whereas exposure to IGF-I alone resulted in about a 25% increase in cellular growth rates, using smooth muscle cells.

In a second embodiment, the IGF binding protein (stimulatory form) and the IGF-I are pre-mixed prior to their addition to the target cells.

The IGF binding protein (stimulatory form) of the present invention is obtained, in one embodiment, in a substantially purified form by isolation from human tissues. In particular, a substantially purified IGF binding protein (stimulatory form) may be isolated from human extracellular fluids. These extracellular fluids include amniotic and spinal fluids. In a preferred form of this embodiment, the IGF binding protein (stimulatory form) is isolated from human amnionic fluid. A detailed methodology for the isolation of this particular IGF binding protein (stimulatory form) from extracellular fluids is set forth in Example 1, which follows.

In an alternate embodiment, the IGF binding protein (stimulatory form) of the present invention may be isolated in a substantially purified form from media conditioned by human cell lines. The cell lines include, but are not limited to, fibroblast cell lines, such as GMI0, and breast carcinoma cell lines such as MDA-231. A detailed methodology for the isolation of this particular IGF binding protein (stimulatory form) from fibroblast conditioned media is set forth in Example 5, which follows. This second IGF binding protein (stimulatory form) is closely related to but not identical to the protein isolatable from extracellular fluids.

When either type of IGF binding protein (stimulatory form) is being isolated, a series of tests have been developed to assist in determining that the correct protein has been isolated. These tests may be used independently or may be used in some combination to confirm the isolation of IGF binding protein (stimulatory form).

The first of these tests is to determine whether the isolated protein can bind IGF-I. One method for making this determination is described in Clemmons, D. in J. Clin. Invest. 77:1548–1556 (1986), the disclosure of which is expressly incorporated herein by reference. A second test is the ability to promote the effects IGF-I in a synergistic manner. One method for conducting this test is set forth in Example 2.

A third test is the ability of the isolated protein to react with an antibody raised against IGF-I binding protein (stimulatory form). In particular, polyclonal antibodies may be raised against this protein by any of the methods known to those of ordinary skill in the art, particularly in light of the teachings contained herein and used to confirm the identity of binding protein.

In the above description, the term "substantially purified" has been used. For the purposes of this application, this term is intended to mean that the protein is at least about 50% free of contaminants as determined by SDS PAGE. Preferably, the protein is at least about 75% free of contaminants and most preferably at least about 90% free of contaminants. It should be noted that the IGF binding protein previously isolated occurs naturally as a mixture of IGF binding protein (inhibitory form) and (stimulatory form). Thus, while the IGF binding proteins described herein are "substantially pure" when at least about 50% free of contaminants, these binding proteins should be at least about 75% separated from each other. The isolation and purification of the IGF binding proteins of the present invention are described in Example 1.

The sequence of an IGF binding protein is described in Example 3. Isolation of the gene encoding an IGF binding protein is described in Example 4.

In another embodiment, the present invention relates to the portable DNA sequences encoding insulin-like growth factor binding proteins. These portable DNA sequences are capable of directing production of human IGF binding proteins in a variety of host microorganisms and eukaryotic cells. "Portable DNA sequence" in this context is intended to refer either to a full length DNA clone or synthetically-produced analog or any combination of the two. For the purposes of this specification, "human insulin-like growth factor binding proteins" are intended to mean the primary structure of the proteins as defined by the codons present in the deoxyribonucleic acid sequence which directs intracellular production of the amino acid sequences, and which may or may not include post-translational modifications. The "human insulin-like growth factor binding proteins produced by the present invention are at least 50%, preferably at least 60% and most preferably at least 80% identical to the naturally-occurring human proteins. The percent identity as discussed herein is calculated as the percentage of amino acid residues found in the smaller of the two sequences that align with identical amino acid residues in the sequence being compared when four gaps per 100 amino acids are allowed to assist in alignment.

In a preferred embodiment, the portable DNA sequences are capable of directing production of IGF binding protein. In a particularly preferred embodiment, the portable DNA sequences are capable of directing production of an IGF binding protein biologically equivalent to that previously isolated from human amniotic fluid or fibroblast conditioned medium. By "biologically equivalent," as used herein in the specification and claims, it is meant that the IGF binding protein produced using a portable DNA sequence of the present invention is activatable to a form capable of inducing a potentiated or inhibited cell growth activity qualitatively and quantitatively equivalent to that produced by IGF binding proteins isolated from human amniotic fluid or fibroblast conditioned media.

As noted previously, the portable DNA sequences of the present invention may be synthetically created. It is believed that the means for synthetic creation of these polynucletide sequences are generally known to one of ordinary skill in the art, particularly in light of the teachings contained herein. As an example of the current state of the art relating to polynucleotide synthesis, one is directed to Matteucci, M. D. and Caruthers, M. H., in J. Am. Chem. Soc. 103:3185 (1981) and Beauchee, S. L. and Caruthers, M. H. in Tetrahedron Lett. 22:1859 (1981), each of which is specifically incorporated herein by reference.

Additionally, the portable DNA sequence may be a fragment of a natural sequence, i.e., a fragment of a polynucleotide which occurred in nature and which has been isolated and purified for the first time by the present inventors. In one embodiment, the portable DNA sequence is a restriction fragment isolated from a CDNA library. In this preferred embodiment, the cDNA library is created as described in Example 4.

In an alternative embodiment, the portable DNA sequence is isolated from a human genomic library. An example of such a library useful in this embodiment is set forth by Lawn et al. in cell 15:1157–1174 (1978), specifically incorporated herein by reference.

As noted above, the present invention relates to a series of vectors, each containing at least one of the portable DNA sequences described herein. It is contemplated that additional copies of the portable DNA sequence may be included in a single vector to increase the host organism or eukaryotic cell's ability to produce large quantities of the desired IGF binding protein. In addition, the cloning vectors within the scope of the present invention may contain supplemental nucleotide sequences preceding or subsequent to the portable DNA sequence. The supplemental sequences are those that will not interfere with transcription of the portable DNA sequence and will, in some instances as set forth more fully below, enhance transcription, translation, or the ability of the primary amino acid structure of the resultant IGF finding protein to assume a functional tertiary form.

It is to be understood that additional cloning vectors may now exist or will be discovered which have the above-identified properties and are therefore suitable for use in the present invention. These vectors are also contemplated as being within the scope of the disclosed series of cloning vectors into which the cDNA sequences may be introduced, along with any necessary operational elements, and which altered vectors are then included within the scope of the present invention and would be capable of being used in the recombinant-DNA method set forth more fully below. Certain preferred vectors with these characteristics are described in the Examples which follow.

I. Expression of Genes for IGF Binding Protein in Microorganism Cells

Sections A, B and C which follow immediately below refer to the production of portable DNA sequences in microorganism hosts.

A. Characteristics of Preferred Vectors for Microorganism

Certain embodiments of the present invention are envisioned which employ known or currently undiscovered vectors which would contain one or more of the cDNA sequences described herein.

Vectors having the foregoing characteristics and constructed by these methods are set forth in Example 9. These include pJU1020, pJU1021, and pJU1022. The details for the construction of these preferred plasmids are described more fully in the Examples and Figures.

C. Host Microorganism

The vectors and methods disclosed are suitable for use in host cells over a wide range of prokaryotic and eukaryotic organisms. Prokaryotes are preferred for the cloning of DNA sequences and for the expression of the gene. The *E. coli* strains JM105, JM107 and JM109 (available from Pharmacia), as well as Bacillus and Pseudomonas species, may be used for expression of the gene. In addition to prokaryotes, eukaryotic microbes such as *Saccharomyces cerevisiae* may be used for expression of the gene.

*E. coli* Vectors

In general, plasmid vectors containing operational elements which are derived from *E. coli*. In a preferred embodiment of the present invention, *E. coli* is transformed using plasmids created from pJU1003 and PCJXi2. Table I indicates the list of host organisms and the compatible vectors.

TABLE 1

| HOSTS | REGULATED PROMOTERS | INDUCER | TRANSCRIPTION TERMINATOR | MRNA STABILIZATION | TRANSCRIPTIONAL START SITE & LEADER PEPTIDE | MARKER | RS BINDING SITE |
|---|---|---|---|---|---|---|---|
| *E. coli* | Lac[1], Tac[2] Lambda pL Trp[5] | IPTG increased temperature IAA addition or tryptophan depletion | rrnB[6] rrnC[7] | ompA[8] lambda int[9] trp[10] | bla[11] ompA[12] phos | ampicillin[14] tetracycline[14,15] chloroamphenical[16] | 1 |
| Bacillus | *alpha amylase[17] *subtilisin[18] *p-43[19] spac-I[26] | IPTG | *E. coli* rrn rrn BT.T[20] | | B. amy neutral protease[21] B. amy alpha-amylase[22] B. subt. subtilisin[23] | Kan[r 24] Cam[r 25] | B. amy neutral protease B. amy alpha-amylase[22] |
| Pseudomonas | Trp[27] (*E. coli*) Lac (*E. coli*) Tac (*E. coli*) | IAA addition, or tryptophan depletion IPTG | | | phospholipase C[28] exotoxin A[29] | sulfonamide[30] streptomycin[30] | Trp (*E. coli*) |
| Yeast | Gal 1[31], 10[32] Adh I[33], II[34] Pho 5 | Glucose depletion and galactose Glucose depletion Phosphate depletion | Cyc 1 Una Alpha factor Sac 2 | | Invertase[36] Acid phosphatase[36] Alpha Factor | Ura 3[37] Leu 2[38] His 3 Tap 1 | |

*non-regulated
[1]Backman, K., Ptashne, M. and Gilbert, W. Proc. Natl. Acad. Sci. USA 73, 4174–4178 (1976).
[2]de Boer, H. A., Comstock, L. J., and Vasser, M. Proc. Natl. Acad. Sci. USA 80, 21–25 (1983).
[3]Shimatake, H. and Rosenberg, M. Nature 292, 128–132 (1981).
[4]Derom, C., Gheysen, D. and Fiers, W. Gene 17, 45–54 (1982).
[5]Hallewell, R. A. and Emtage, S. Gene 9, 27–47 (1982).
[6]Brosius, J., Dull, T. J., Sleeter, D. D. and Noller, H. F. J. Mol. Biol. 148, 107–127 (1981).
[7]Normanly, J., Ogden, R. C., Horvath, S. J. and Abelson, J. Nature 321, 213–219 (1986).
[8]Belasco, J. G., Nilsson, G., von Gabain, A. and Cohen, S. N. Cell 46, 245–251 (1986).
[9]Schmeissner, U., McKenney, K., Rosenberg M. and Court, D. J. Mol. Biol. 176, 39–53 (1984).
[10]Mott, J. E., Galloway, J. L. and Platt, T. EMBO J. 4, 1887–1891 (1985).
[11]Koshland, D. and Botstein, D. Cell 20, 749–760 (1980).
[12]Movva, N. R., Nakamura, K. and Inouye, M. J. Mol. Biol. 143, 317–328 (1980).
[13]Surin, B. P., Jans, D. A., Fimmel, A. L., Shaw, D. C., Cox, G. B. and Rosenberg, H. J. Bacteriol. 157, 772–778 (1984).
[14]Sutcliffe, J. G. Proc. Natl. Acad. Sci. USA 75, 3737–3741 (1998).

TABLE 1-continued

| HOSTS | REGULATED PROMOTERS | INDUCER | TRANSCRIPTION TERMINATOR | MRNA STABILIZATION | TRANSCRIPTIONAL START SITE & LEADER PEPTIDE | MARKER | RS BINDING SITE |
|---|---|---|---|---|---|---|---|

[15] Peden, K. W. C. Gene 22, 277–280 (1983).
[16] Alton, N. K. and Vapnek, D. Nature 282, 864–869 (1979).
[17] Yang, M., Galizzi, A., and Henner, D. Nuc. Acids Res. 11(2), 237–248 (1983).
[18] Wong, S. -L., Price, C. W., Goldfarb, D. S., and Doi, R. H. Proc. Natl. Acad. Sci. USA 81, 1184–1188 (1984).
[19] Wang, P. -Z., and Doi, R. H. J. Biol. Chem. 259, 8619–8625, (1984).
[20] Lin, C. -K., Quinn, L. A. Rodriquez, R. L. J. Cell Biochem. Suppl. (9B), p. 198 (1985).
[21] Vasantha, N., Thompson, L. D., Rhodes, C., Banner, C., Nagel, J., and Filpula, D. J. Bact. 159(3), 811–819 (1984).
[22] Palva, I., Sarvas, M., Lehtovaara, P., Sibazkov, M., and Kaariainen, L. Proc. Natl. Acad. Sci. USA 79, 5582–5586 (1982).
[23] Wong. S. -L., Pricee, C. W., Goldfarb, D. S., and Doi, R. H. Proc. Natl. Acad. Sci. USA 81, 1184–1188 (1984).
[24] Sullivan, M. A., Yasbin, R. E., and Young, F. E. Gene 29, 21–46 (1984).
[25] Vasantha, N., Thompson, L. D., Rhodes, C., Banner, C. Nagle, J., and Filpula, D. J. Bact. 159(3), 811–819 (1984).
[26] Yansura, D. G. and Henner, D. J. PNAS 81, 439–443 (1984).
[27] Gray, G. L., McKeown, K. A., Jones, A. J. S., Seeburg, P. H. and Heyneker, H. L. Biotechnology, 161–165 (1984).
[28] Lory, S., and Tai, P. C. Gene 22, 95–101 (1983).
[29] Liu, P. V. J. Infect. Dis. 130 (suppl), 594–599 (1974).
[30] Wood, D. G., Hollinger, M. F., and Tindol, M. B. J. Bact. 145, 1448–1451 (1981).
[31] St. John, T. P. and Davis, R. W. J. Mol. Biol. 152, 285–315 (1981).
[32] Hopper, J. E., and Rowe, L. B. J. Biol. Chem. 253, 7566–7569 (1978).
[33] Denis, C. L., Ferguson, J. and Young, E. T. J. Biol. Chem. 258, 1165–1171 (1983).
[34] Lutsdorf, L. and Megnet, R. Archs. Biochem. Biophys. 126, 933–944 (1968).
[35] Meyhack, B., Bajwa, N., Rudolph, H. and Hinnen, A. EMBO. J. 6, 675–680 (1982).
[36] Watson, M. E. E. Nucleic Acid Research 12, 5145–5164 (1984).
[37] Gerband, C. and Guerineau, M. Curr. Genet. 1, 219–228 (1980).
[38] Hinnen, A., Hicks, J. B. and Fink, G. R. Proc. Natl. Acad. Sci. USA 75, 1929–1933 (1978).
[39] Jabbar, M. A., Sivasubramanian, N. and Nayak, D. P. Proc. Natl. Acad. Sci. USA 82, 2019–2023 (1985).

1. Pseudomonas Vectors

In addition to the vectors listed in Table I, several vector plasmids which autonomously replicate in a broad range of Gram negative bacteria are preferred for use as cloning vehicles in hosts of the genera Pseudomonas. These are described by Tait, R. C., Close, T. J., Lundquist, R. C., Hagiya, M., Rodriguez, R. L., and Kado, C. I. in Biotechnology, May, 1983, pp. 269–275; Panopoulos, N.J. in Genetic Engineering in the Plant Sciences, Praeger Publishers, New York, N.Y., pp. 163–185, (1981); and Sakaguchi, K. in Current Topic in Microbiology and Immunology 96:31–45, (1982), each of which is specifically incorporated herein by reference.

One particularly preferred construction would employ the plasmid RSF1010 and derivatives thereof as described by Bagdasarian, M., Bagdasarian, M. M., Coleman, S., and Timmis, K. N. in Plasmids of Medical Environmental and Commercial Importance, Timmis, K. N. and Puhler, A. eds., Elsevier/North Holland Biomedical Press, (1979), specifically incorporated herein by reference. The advantages of RSF1010 are that it is relatively a small, high copy number plasmid which is readily transformed into and stably maintained in both E. coli and Pseudomonas species. In this system, it would be preferred to use the Tac expression system as described for Escherichia, since it appears that the E. coli trp promoter is readily recognized by Pseudomonas RNA polymerase as set forth by Sakaguchi, K. in Current Topics in Microbiology and Immunology 96:31–45 (1982) and Gray, G. L., McKeown, K. A., Jones, A. J. S., Seeburg, P. H., and Heyneker, H. L. in Biotechnology February 1984, pp. 161–165, both of which are specifically incorporated herein by reference. Transcriptional activity may be further maximized by requiring the exchange of the promoter with, e.g., an E. coli or P. aeruginosa trp promoter. Additionally, the lacI gene of a lacI$^q$ strain of E. coli would also be included in the plasmid to effect regulation.

Translation may be coupled to translation initiation for any of the E. coli proteins as described in the Examples, as well as to initiation sites for any of the highly expressed proteins of the host to cause intracellular expression of the inhibitor.

In those cases where restriction minus strains of a host Pseudomonas species are not available, transformation efficiency with plasmid constructs isolated from E. coli are poor. Therefore, passage of the Pseudomonas cloning vector through an r– m+ strain of another species prior to transformation of the desired host, as set forth in Bagdasarian, M., et al., Plasmids of Medical, Environmental and Commercial Importance, pp. 411–422, Timmis and Puhler eds., Elsevier/North Holland Biomedical Press (1979), specifically incorporated herein by reference, is desired.

2. Bacillus Vectors

Furthermore, a preferred expression system in hosts of the genera Bacillus involves using plasmid pUB110 as the cloning vehicle. As in other host vector systems, it is possible in Bacillus to express the IGF binding protein of the present invention as either an intracellular or a secreted protein. The present embodiments include both systems. Shuttle vectors that replicate in both Bacillus and E. coli are available for constructing and testing various genes as described by Dubnau, D., Gryczan, T., Contente, S., and Shivakumar, A. G. in Genetic Engineering, Vol. 2, Setlow and Hollander eds., Plenum Press, New York, N.Y., pp. 115–131, (1980), specifically incorporated herein by reference. For the expression and secretion of the IGF binding protein from B. subtilis, the signal sequence of alpha-amylase is preferably coupled to the coding region for the protein. For synthesis of intracellular inhibitor, the portable DNA sequence will be translationally coupled to the ribosome binding site of the alpha-amylase leader sequence.

Transcription of either of these constructs is preferably directed by the alpha-amylase promoter or a derivative thereof. This derivative contains the RNA polymerase recognition sequence of the native alpha-amylase promoter but incorporates the lac operator region as well. Similar hybrid promoters constructed from the penicillinase gene promoter and the lac operator have been shown to function in Bacillus hosts in a regulatable fashion as set forth by Yansura, D. G. and Henner in Genetics and Biotechnology of Bacilli, Ganesan, A. T. and Hoch, J. A., eds., Academic Press, pp.

249–263, (1984), specifically incorporated by reference. The lacI gene of a lacI$^q$ strain of *E. coli* would also be included in the placement to effect regulation.

3. Clostridium Vectors

One preferred construction for expression in Clostridium is in plasmid pJU12, described by Squires, C. H. et al. in J. Bacteriol. 159:465–471 (1984) and specifically incorporated herein by reference, transformed into *C. perfringens* by the method of Heefner, D. L. et al. as described in J. Bacteriol. 159:460–464 (1984), specifically incorporated herein by reference. Transcription is directed by the promoter of the tetracycline resistance gene. Translation is coupled to the Shine-Dalgarno sequences of this same $tet^r$ gene in a manner strictly analogous to the procedures outlined above for vectors suitable for use in other hosts.

4. Yeast Vectors

Maintenance of foreign DNA introduced into yeast can be effected in several ways as described by Botstein, D., and Davis, R. W., in *The Molecular Biology of the Yeast Saccharomyces,* Cold Spring Harbor Laboratory, Strathern, Jones and Broach, eds., pp. 607–636 (1982), specifically incorporated herein by refrence. One preferred expression system for use with host organisms of the genus Saccharomyces harbors the IGF binding protein gene on the 2 micron plasmid. The advantages of the 2 micron circle include relatively high copy number and stability when introduced into cir° strains. These vectors preferably incorporate the replication origin and at least one antibiotic resistance marker from pBR322 to allow replication and selection in *E. coli.* In addition, the plasmid will preferably have 2 micron sequences and the yeast LEU2 gene to serve the same purposes in LEU2 defective mutants of yeast.

This invention also relates to a recombinant-DNA method for the production of IGF binding protein. Generally, this method includes:

(a) preparation of a portable DNA sequence capable of directing a host microorganism to produce IGF binding protein;

(b) cloning the portable DNA sequence into a vector capable of being transferred into and replicating in a host microorganism, such vector containing operational elements for the portable DNA sequence;

(c) transferring the vector containing the portable DNA sequence and operational elements into a host microorganism capable of expressing the IGF binding protein;

(d) culturing the host microorganism under conditions appropriate for amplification of the vector and expression of IGF binding protein; and (e) in either order:

(i) harvesting the IGF binding protein; and (ii) causing the IGF binding protein to assume an active tertiary structure.

In this method, the portable DNA sequences are those synthetic or naturally-occurring polynucleotides described above. In a preferred embodiment of the present method, the portable DNA sequence has the nucleotide sequence as defined by the cDNA whose isolation is described in Example 4.

The vectors contemplated as being useful in the present method are those described above. In a preferred embodiment, the cloning vector containing the Col. E1 origin of replication, a T7 promoter and a marker for tetracycline resistance is to be used. The gene for IGF binding protein fragment of T7 is translationally coupled to a G10 protein.

The vector thus obtained is then transferred into the appropriate host microorganism, for instance *E. coli* containing a chromosomal copy of gene 1 from coliphage T7 and transcribed from the lac promoter. It is believed that any microorganism having the ability to take up exogenous DNA and express those genes and attendant operational elements may be chosen. It is preferred that the host microorganism be an anaerobe, facultative anaerobe or aerobe. Particular hosts which may be preferable for use in this method include yeasts and bacteria. Specific yeasts include those of the genus Saccharomyces, and especially *Saccharomyces cerevisiae.*

Specific bacteria include those of the genera Bacillus and Escherichia and Pseudomonas. Various other preferred hosts are set forth in Table I, supra. In other, alternatively preferred embodiments of the present invention, *Bacillus subtilis, Escherichia coli* or *Pseudomonas aeruginosa* are selected as the host microorganisms.

After a host organism and vector have been chosen, the vector is transferred into the host organism using methods generally known by those of ordinary skill in the art. Examples of such methods may be found in *Advanced Bacterial Genetics* by R. W. Davis et al., Cold Spring Harbor Press, Cold Spring Harbor, N.Y., (1980), which is specifically incorporated herein by reference. It is preferred, in one embodiment, that the transformation occur at low temperatures, as temperature regulation is contemplated as a means of regulating gene expression through the use of operational elements as set forth above. In another embodiment, if osmolar regulators have been inserted into the vector, regulation of the salt concentrations during the transformation would be required to insure appropriate control of the synthetic genes.

If it is contemplated that the recombinant IGF binding protein will ultimately be expressed in yeast, it is preferred that the cloning vector first be transferred into *Escherichia coli,* where the vector would be allowed to replicate and from which the vector would be obtained and purified after amplification. The vector would then be transferred into the yeast for ultimate expression of the IGF binding protein.

The host microorganisms are cultured under conditions appropriate for the expression of IGF binding protein. These conditions are generally specific for the host organism, and are readily determined by one of ordinary skill in the art, in light of the published literature regarding the growth conditions for such organisms, for example *Bergey's Manual of Determinative Bacteriology,* 8th ed., Williams & Wilkins Company, Baltimore, Md., which is specifically incorporated herein by reference.

Any conditions necessary for the regulation of the expression of the DNA sequence, dependent upon any operational elements inserted into or present in the vector, would be in effect at the transformation and culturing stages. In one embodiment, the cells are grown to a high density in the presence of appropriate regulatory conditions which inhibit the expression of the DNA sequence. When optimal cell density is approached, the environmental conditions are altered to those appropriate for expression of the portable DNA sequence. It is thus contemplated that the production of IGF binding protein will occur in a time span subsequent to the growth of the host cells to near optimal density, and that the resultant IGF binding protein will be harvested at some time after the regulatory conditions necessary for its expression were induced.

In a preferred embodiment of the present invention, the recombinant IGF binding protein is purified subsequent to harvesting and prior to assumption of its active structure.

This embodiment is preferred as the inventors believe that recovery of a high yield of re-folded protein is facilitated if the protein is first purified. However, in one preferred, alternate embodiment, the IGF binding protein may be allowed to re-fold to assume its native structure prior to purification. In yet another preferred, alternate embodiment, the IGF binding protein is caused to assume its re-folded state upon recovery from the culturing medium.

In certain circumstances, the IGF binding protein will assume its proper, active structure upon expression in the host microorganism and transport of the protein through the cell wall or membrane or into the periplasmic space. This will generally occur if DNA coding for an appropriate leader sequence has been linked to the DNA coding for the recombinant protein. The preferred IGF binding protein of the present invention will assume their mature, active form upon translocation out of the inner cell membrane. The structures of numerous signal peptides have been published, for example by Marion E. E. Watson in *Nuc. Acid Res.,* 12:515–5164 (1984), specifically incorporated herein by reference. It is intended that these leader sequences, together with portable DNA, will direct intracellular production of a fusion protein which will be transported through the cell membrane and will have the leader sequence portion cleaved upon release from the cell.

In a preferred embodiment, the signal peptide of the *E. coli* OmpA protein is used as a leader sequence and is located in a position contiguous with the portable DNA sequence coding for the IGF binding protein structure.

Additionally preferred leader sequences include those of beta-lactamase, carboxypeptidase G2 and the human signal protein. These and other leader sequences are described.

If the IGF binding protein does not assume its proper structure, any disulfide bonds which have formed and/or any noncovalent interactions which have occurred will first be disrupted by denaturing and reducing agents, for example, guanidinium chloride and beta-mercaptoethanol, before the IGF binding protein is allowed to assume its active structure following dilution and oxidation of these agents under controlled conditions.

The transcription terminators contemplated herein serve to stabilize the vector. In particular, those sequences as described by Gentz et al., in Proc. Natl. Acad. Sci. USA 78: 4936–4940 (1981) specifically incorporated herein by reference, are contemplated for use in the present invention.

II. Expression of Genes for IGF Binding Protein in Animal Cells

Methods comparable to the foregoing for the expression of IGF being proteins in higher eukaryotic cells are set forth in Example 6.

The following examples illustrate various presently preferred embodiments of the present invention. The publications provided in these examples are specifically incorporated by reference herein.

EXAMPLES

Example 1

Protein Preparation

A. Materials

Human amniotic fluid was obtained from discarded amniocentesis samples. Ammonium sulfate and sodium chloride were purchased from EM Sciences, Cherry Hill, N.J. DEAE cellulose, ammonium persulfate, sodium thiocyanate, Sephadex G-100, polyethylene glycol (MW 8,000) and ammonium carbonate were purchased from Sigma Chemical Co., St. Louis, Mo. Phenyl sepharose CL-4-B was purchased from Pharmacia, Piscataway, N.J. DEAE cellulose was obtained from Whatman and the C-4 reverse phase HPLC column from Vydac, Hesperia, Calif. Acetonitrile, Gel Code® silver stain kit and trifloroacetic acid were purchased from Pierce Chemical Co., Rockville, Ill. Tris, SDS and TEMED were obtained from Bethesda Research Laboratories, Gaithersburg, Md. Glycine, bromophenol blue, Servalyt® isoelectric focusing Precotes® and glycerol were obtained from Serva, Heidelberg, Germany. Tissue culture plates were purchased from Falcon Labware Division, Becton Dickinson, Oxnard, Calif.

B. Purification of the Stimulators and Inhibiting IGF Binding Protein From Amniotic Fluid Crude amniotic fluid (230 ml) was equilibrated with ammonium sulfate (33% wt/vol) by the addition of 45 gms and the solution was stirred for 30 min at 8° C. The mixture was centrifuged 27,000×g for 20 min then the pellet reconstituted in 50 cc of 0.05 M Tris HCL pH 7.4. This solution was adjusted to 50% ammonium sulfate stirred for 30 min and the centrifugation step repeated. The pellet was resuspended in 50 cc of 0.05 M Tris pH 7.4 and 1.2 ml of saturated ammonium sulfate added to achieve a final concentration of 0.14 M. This solution was applied to a phenyl sepharose column (2.2×15.0 cm) that had been previously equilibrated with 0.05 M Tris pH 7.4 in 10% ammonium sulfate. Following sample loading the column was washed with the loading buffer until the absorbance (280 nM) return to baseline. The column was eluted with step gradients containing (1) 0.05 M Tris, pH 7.4, 0.5 M sodium thiocyanate, pH 7.4; (2) 0.05 M Tris, pH 7.4; (3) 0.02 M Tris, pH 9.0; and (4) $H_2O$. Each fraction was assayed for IGF-I binding activity as described below in Example I.F. The active fractions were pooled, the pH adjusted to 7.2 with 1.0 M acetic acid and the solution applied directly to a DEAE cellulose column that had been equilibrated with 0.01 M $(NH_4)_2$ $CO_3$, 0.01 M NaCl, pH 7.2. After sample application the column was washed extensively with the equilibration buffer until the absorbance (280 nM) returned to baseline. The column was eluted with step salt gradients containing 0.1, 0.25, and 0.5 and 1.0 M NaCl in the loading buffer. The fractions were assayed for IGF binding activity as described. Greater than 80% of the activity eluted with 100 or 250 mM NaCL. These two peaks, termed B and C, were purified separately. 1.5 cc of the peak B pool was applied to a C-4 Vydac reverse phase HPLC column (0.46×25 cm) that had been equilibrated with 0.04% TFA. The mobile phase was run isocratically for 5 min then a linear gradient from 0–100% acetonitrile plus 0.04% TFA was run over 25 min. The IGF binding protein activity of each fraction was determined and the active fractions pooled and stored at −20° C.

Pool C from the ion exchange column was first purified by Sephadex G-100 column chromatography. Ten cc of pool C was applied to a 2.2×90 cm column that had been equilibrated with 0.01 $(NH_4)_2$ $CO_3$, 0.05 M NaCl, pH 7.2 and approximately 9 cc fractions were collected. The IGF-I binding activity was determined and the active fraction pool applied directly to the reverse phase C-4 column as stated previously. Elution conditions that were identical to those stated previously were used.

C. Physicochemical Analyses

The purity of both peaks B and C was determined by SDS polyacrylamide gel electrophoresis. The running gel was 12% acrylamide containing 0.375 M Tris, pH 8.8 and the stacking gel was 4% acrylamide in 0.125 M Tris, pH 6.8, 0.1–10 ug of sample was diluted to 75 ul in 0.1 M Tris, pH 6.8, 10% glycerol, 5% SDS and 0.02% bromophenol blue and the samples were heated to 100° C. for 5 min. The supernatants were clarified, the gel lanes loaded, and the proteins separated for 14 hours at 65 volts. Silver staining was performed using Gel code® silver staining kit. The lower limit of detection of the technique was 25 ng as determined using known protein standards. Gels were fixed for 5 hours in 50% ethanol, 5% acetic acid and were then washed with 4 changes of deionized water over a period of 4 hours. The final water wash was replaced by the silver solution (20 ml silver concentrate plus 280 ml water) for 60 minutes with gentle shaking. After a brief $H_2O$ rinse, the reducer solution, containing reducer aldehyde plus reducer base (mixed just prior to use) was added and allowed to gently shake for 8–10 minutes until protein bands of sufficient intensity were observed. The reducer solution was replaced by three successive 30 minute washes with the stabilizer solution containing 20 ml stabilizer base plus 880 ml $H_2O$.

D. Amino Acid Composition and Sequence Analysis 500 ng each protein was lyophylized under 6N HCl containing 0.1% phenol for one hour at 150° C. in vacuo. The amino acids were derivitized with phenylisothiocyanate and the labelled amino acids separated using a NovaPak-C18 Reverse phase. Determination of amino acid sequence is described in Example 3.

E. Determination of Carbohydrate Content

To determine if either peak B or C contained carbohydrate, 5.0 ug of each peak was loaded on a 12% SDS polyacrylamide gel and separated for 14 hours as described previously. Fetuin was run in parallel as a standard. The gel was fixed 10% acetic acid/25% isopropanol. The gel was then washed sequentially with (1) 0.5% periodic acid; (2) 0.5% sodium arsenite; (3) 0.1% sodium arsenite 5% acetic acid; (4) 5% acetic acid; (5) Schiff's reagent; and (6) 0.6% sodium metabisulfite/0.01 M HCL and stained for 2 hours.

To further determine if either peak B or peak C contained carbohydrate 2.0 ug of each protein was applied to a concanavalin-A-sepharose column that had been equilibrated in 0.02 Tris, pH 7.5, 2 mM $CaCL_2$ and 2 mM $MgCl_2$. The column was slowly loaded over 2 hours and allowed to stand for 45 min at 22° C. The column was further washed with 20 ml starting buffer and then the glycoproteins eluted with 10 ml of 0.02 M Tris, pH 7.5 containing 0.5 M methyl-D-mannoside and 0.1 M NaCl. After one hour the column was eluted. The column was then refilled with the same solution and allowed to stand overnight at 8° C. and then eluted. The column was further eluted with 0.02 M Tris, pH 7.5 containing 0.5 M methyl-D-mannoside and 0.1 M NaCl, and the fractions were tested for IGF binding activity as described previously.

F. $^{125}$I-IGF-I Binding Capacity

IGF-I binding activity of the column fractions was determined as follows: 10 ul of each fraction was incubated with 40,000 CPM $^{125}$I-IGF-I (150 uCi/ug) for 60 minutes at 22° C. in 0.1 M Hepes, 0.1% BSA, 0.01% Triton X-100, 44 mM $NaHCO_3$ 0.02%, $NaN_3$, pH 6.0 (250 ul total volume). The IGF-I was iodinated as described by E'Ercole, A. J., Underwood, L. E., Van Wyk, J. J., Decedue, C. J., and Foushee, D. B. (1976) in Growth Hormone and Related Peptides (Pecili, A., and Mueller, E. E., eds.) pp. 190–201, Excerpta Medica, Amsterdam, specifically incorporated herein by reference. Bound and free $^{125}$I-IGF-I were separated by adding 1% immune serum globulin and 500 ul of 25% polyethylene glycol (MW 8,000) to a final concentration of 12.5%. The mixture was centrifuged at 8,000×g for 10 minutes then the pellet washed with 6.25% PEG and the final pellet counted in a gamma spectrometer. Each pool of active fraction was reassayed at several concentrations and the binding capacity compared to a human amniotic fluid standard. The data were used to assign a unit value to each pool. One unit was the quantity of material necessary to achieve half maximal IGF-I binding.

To determine the binding capacity and affinity of the pure IGF binding protein for IGF-I, radiolabelled IGF-I (40,000 cpm/tube) was incubated with 10 ng/ml of each binding protein and increasing concentrations of unlabelled IGF-I in 0.5 ml of 0.02 M phosphate buffer, pH 7.4. After 48 hours at 4° C. the bound and free $^{125}$I-IGF-I were separated by adding a 1:1,000 dilution of a rabbit antibody against the binding protein and the incubation continued for 12 hours. At that time, 2 ul of goat antirabbit serum was added and the mixture incubated for one hour at 22° C. then 2 ul of normal rabbit serum was added and the mixture incubated for an additional hour. The bound and free growth factor were separated by centrifugation at 8,000×g for 10 minutes.

G. Determination of $^3$H-Thymidine Incorporation into DNA

The biologic activity of pure peak B and C material was assessed by determining the capacity of each to stimulate DNA synthesis in porcine aortic smooth muscle cells. The smooth muscle cells were isolated and maintained in stock cultures as described by Ross, R. (1971) J.Cell Biol. 50, 172–186, specifically incorporated herein by reference. The cells from stock cultures were subcultred in microtest 96-well plates (Falcon 3004) by plating at 8,000 cells/well in DMEM (Gibco) containing 10% fetal bovine serum. Five days after plating the walls were washed once with serum free DMEM then test factor added to each well on 0.2 ml DMEM supplemented with 1% platelet poor plasma (PPP) and 0.5 uCi $^3$H-thymidine. PPP was prepared as described by Clemmons, D. R. (1983) J. Cell Physiol. 114, 61–67, specifically incorporated herein by reference. After 36 hours of incubation the wells are washed twice with Ringer's bicarbonate, twice with 5% TCA (4° C.) then the DNA extracted twice with 0.4 ml of 0.3 N NaOH and $^3$H-thymidine incorporation determined by liquid scintillation counting.

H. Isoelectric Focusing

To determine their isoelectric points 2.5 ug of peak B and C proteins were loaded on to precast isoelectric focusing plates, pH 3–10, (Servalyt® Precotes®). 20 ug of a known standard was run in a parallel lane. The proteins were electrofocused for 1½ hours at 200 volts then 1½ hours at 1000 volts. The gel was divided into two sections and one-half was fixed 10% TCA then stained with coumassie blue. The other half was cut into 0.5 cm sections and eluted with 0.04% TFA. The eluates were analyzed for IGF binding activity as described previously.

I. Characteristics of IGF Binding Protein

Figure 2:
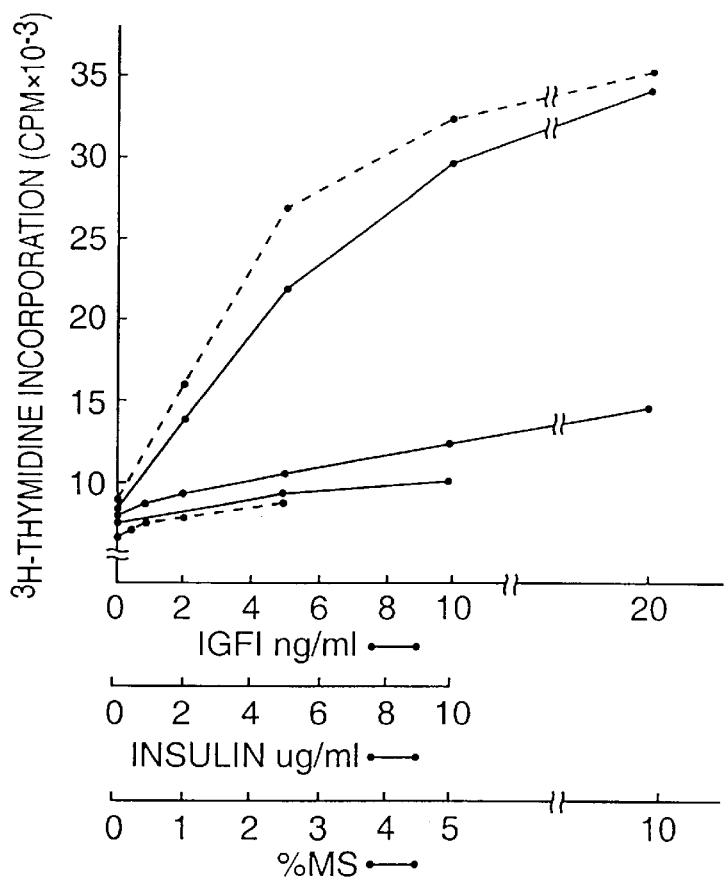
FIG. 2 depicts stimulation of DNA synthesis by the IGF-I binding protein (stimulatory form) in cultured human fibroblasts. Between the 4th and 8th passage, cells were subcultured in 96-well microtest plates in MEM supplemented with 10% calf serum at a density of 8,000 cells/well. Five days after plating, the cultures were washed with serum free MEM then 0.2 ml MEM containing 0.5 uCi $^3$H-thymidine, 1% PPP and the stated concentrations of test substances were added. Increasing concentrations of human serum, IGF-I, insulin, IGF-I plus IGF-I binding protein (stimulatory form) or insulin plus IGF-I binding protein (stimulatory form), were added to quiescent human fibroblast monolayers. After a 36 hour incubation, DNA synthesis determined. The results are expressed as the mean of triplicate cultures.
Figure 3:
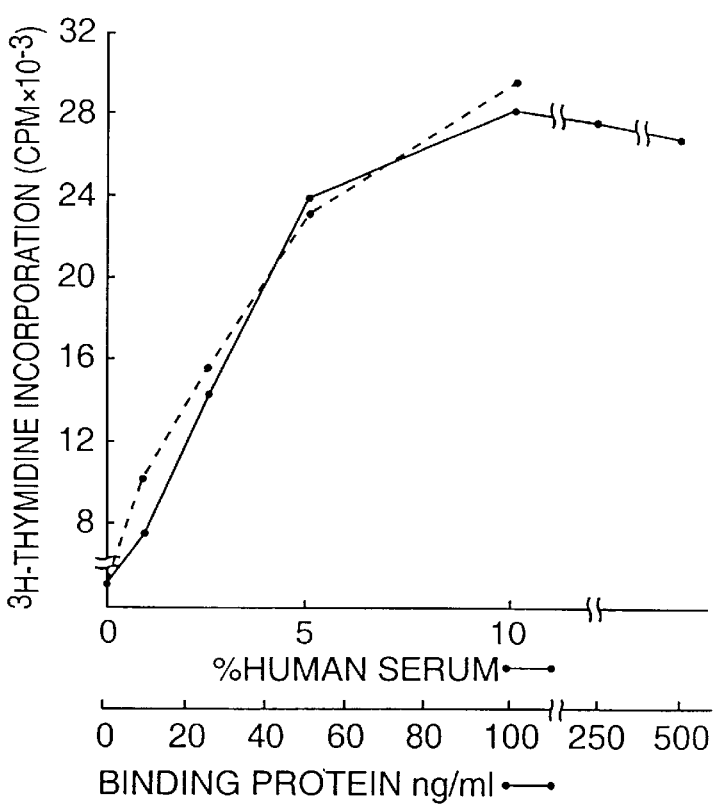
FIG. 3 depicts concentration dependent increases in the smooth muscle cell DNA synthesis in response to the IGF-I binding protein (stimulatory form). Increasing concentrations of the pure IGF-I binding protein (stimulatory form) (10–500 ng/ml) were incubated with 10 ng/ml IGF-I and human 1% PPP. Smooth muscle cell cultures were prepared and $^3$H-thymidine incorporation was determined as described in FIG. 1. The results were expressed as the mean $^3$H-thymidine incorporation of triplicate cultures.
Figures 4A, 4B:
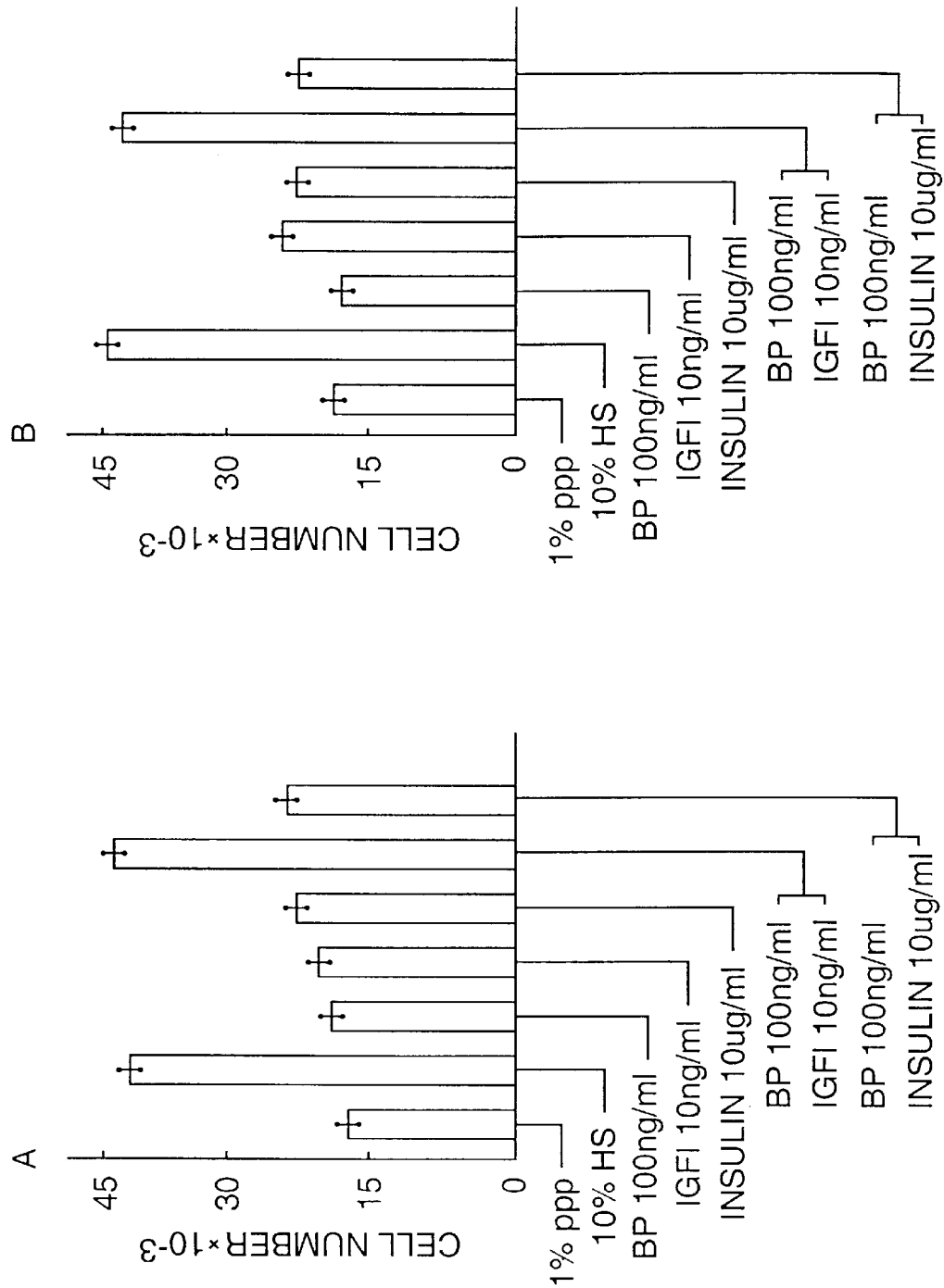
FIG. 4 (Parts A–B) depicts growth of cultured fibroblasts and smooth muscle cells in response to IGF-I and IGF-I binding protein (stimulatory form). Porcine smooth muscle cells (A) and human fibroblasts (B) were plated at 15,000 cells/well on 24-well plates (Falcon, 3004), in MEM plus 10% calf serum (fibroblasts) or DMEM plus 10% fetal calf serum (smooth muscle cells). After 2 hours, the media were changed to MEM or DMEM containing 1% PPP. Following an additional 12 hour incubation, the media were removed and test reagents were added to 0.5 ml DMEM or MEM containing 1% PPP. Following a 48 hour incubation, cell number was determined. The results are expressed as the +1SD of quadruplicate cultures.

Ammonium sulfate precipitation of 230 cc of amniotic fluid resulted in recovery of IGF binding activity in both the 33 and 50% pellets. The majority of the activity was present in the 50% pellet and this was chosen for further purification. During phenyl sepharose chromatography, the majority of contaminating protein eluted with 0.5 M sodium thiocyanate. The peak containing the IGF binding protein eluted with 0.02 M Tris, pH 9.0 and had been purified 9.5-fold. Further purification by ion exchange chromatography resulted in separation of two major peaks of binding activity which eluted at 100 and 250 mM salt (FIG. 2). These peaks (termed peaks B and C) were further purified separately. Peak C material was purified by Sephadex G-100 chromatography. The binding protein activity eluted over a broad peak but was separated from larger molecular weight contaminents (FIG. 3). Sixty ug of G-100 purified material was further purified by reverse phase HPLC using a C-4 column. The active material was eluted as a single peak at 50% acetonitrile and was stable during storage in this buffer for periods of up to 3 months (FIG. 4A). Peak B was purified by the same method as C, using the reverse phase HPLC and this step resulted in a 9.4-fold purification (FIG. 4B).

Figure 5:
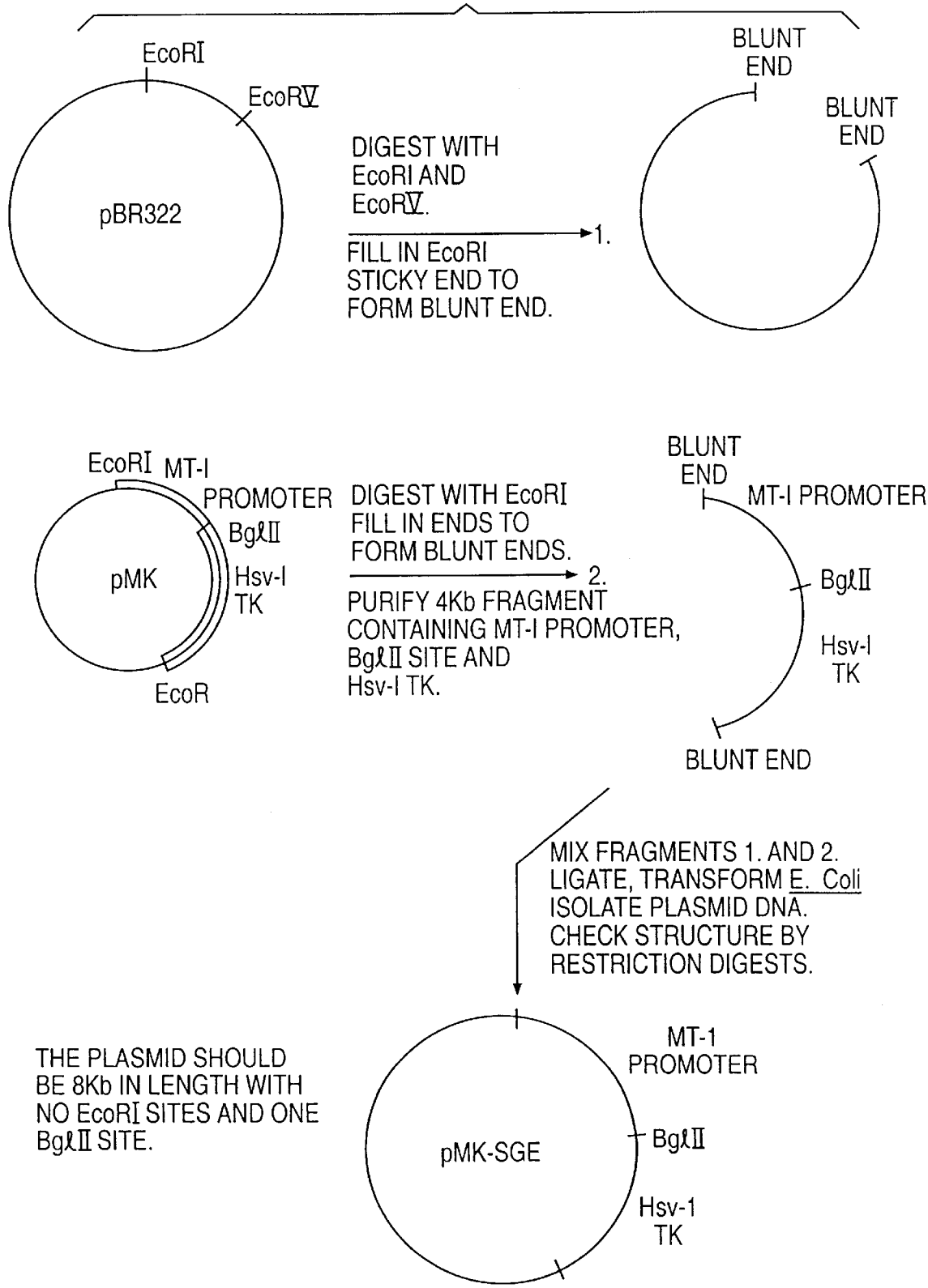
FIG. 5 shows the construction of an expression vector for IGFBP in higher eukaryotic cells.

To determine the purity and estimate the molecular size each protein, the peak C protein at each stage of purification was subjected to polyacrylamide gel electrophoresis under non-reducing conditions followed by silver staining. As shown in FIG. 5 the pure product is 34 Kd and appears as a single band after the final purification step. The phenyl sepharose step appeared to be the most effective procedure for removing the contaminating proteins. Comparison of peak B and peak C showed that they both had identical Rf values on SDS-PAGE. The molecular for weight estimates were 36 kd under non-reducing conditions but increased to 38 kd if the proteins were reduced prior to electrophoresis. When the amino acid compositions of peaks B and C were determined nearly identical amino acid ratios were obtained as set forth in Table II.

TABLE II

AMINO ACID COMPOSITION OF THE IGF-I BINDING PROTEIN

| Amino Acid | Mole % | |
|---|---|---|
| | Peak B | Peak C |
| Aspartic acid and asparagine | 7.3 | 7.6 |
| Glutamic acid and glutamine | 15.1 | 14.9 |
| Serine | 8.5 | 8.7 |
| Glycine | 9.0 | 7.7 |
| Histidine | 2.1 | 2.1 |
| Arginine | 4.9 | 4.6 |
| Threonine | 3.8 | 4.5 |
| Alanine | 12.4 | 11.1 |
| Proline | 8.0 | 8.8 |
| Tyrosine | 2.8 | 2.5 |
| Valine | 3.8 | 3.8 |
| Methionine | 0.7 | 0.6 |
| Cysteine | 4.4[a] | 5.6[a] |
| Isoleucine | 3.6 | 3.9 |
| Leucine | 8.1 | 8.2 |
| Phenylalanine | 2.0 | 1.7 |
| Lysine | 3.7 | 3.8 |
| Tryptophan[b] | — | — |

[a]Based on recovery of cysteine standard following hydrolysis.
[b]Tryptophan is not detectable following hydrolysis.

Reduction and alkylation of peak B with amino acid sequencing showed the following N-terminal sequence shown in Example 3. Both proteins were stable after heating to 100° C. for 10 min and were stable to pH 2.5 but IGF binding activity was destroyed at pH 2.0.

Further physicochemical analysis was performed to determine if carbohydrate side chains were present because it was noted that pure preparations of peak B or C adhered to concanavalin A. When 2 ug of each protein was applied to the con A column, 51% of peak C adhered and was eluted with 0.5 M alphamethylmannoside whereas only 24% of peak B was adherent. In contrast when 20 ug of either peak B or C was stained with Schiff's Base carboyhydrate could not be detected in either protein. Based on the staining intensity of a fetuin standard, the proteins contained less than 0.8% of their weight as carbohydrate.

To determine the affinity of each protein for IGF-I increasing concentrations of unlabelled IGF-I and $^{125}$I-IGF were incubated with peak B or C and the bound complexes immunoprecipitated. The data were analyzed using Scatchard plots. Both proteins have binding characteristics that are consistent with either a two site model with high and low affinity binding sites or a one site model with negative cooperativity. The relative affinities of the high affinity sites of the peak B and C proteins were very similar: 1.06 and $1.1 \times 10^{10}$ L/M respectively.

In spite of their physicochemical similarity the peak B and C materials were found to have markedly distinct biologic properties. Pure peak B material greatly potentiated the smooth muscle cell DNA synthesis response to IGF-I but had no effect alone or with an equivalent concentration of human insulin. In contrast, peak C material inhibited basal and IGF-I stimulated $^3$H-thymidine incorporation and markedly inhibited the response to peak B plus IGF-I. This effect was detectable at concentrations as low as 1.0 ng/ml peak C and was maximal at 20 ng/ml. It appears, therefore, that two forms of the IGF binding protein are present in human amniotic fluid that have markedly different biologic properties when tested in a biologic system.

Example 2

Potentiation of IGF-I by Binding Protein

1. Cell Culture Techniques

Porcine aortic smooth muscle cells were isolated as described by Ross (1971) cited above. Stock cultures were plated at 8,000 cells/cm$^2$ in 10 cm plastic dishes (Falcon Labware Division, Becton Dickinson, Oxnard, Calif. #3001). The stock cultures maintained in Dulbecco's Modified Eagles Medium (DMEM) (Grand Island Biological Co, Grand Island, N.Y.) (Gibco) that was supplemented with 10% fetal bovine serum (FBS) (Hyclone labs, Ogden, Utah). They were passaged every 10–12 days by removing the cells with trypsin 0.03%, EDTA 0.02% (Gibco) and replating at a 1:5 dilution.

All experiments were conducted using cells between the 4th and 7th passages. Individual experiments were conducted using cultures that had been plated at 8,000 cells/well in 96 well microtest plates (Falcon #3004) in 0.2 ml DMEM supplemented with 10% FBS and grown for 5 days. At that time the serum containing media was removed and test substances were added to 0.2 ml DMEM supplemented with 1% human platelet poor plasma (PPP) and 0.5 uCi $^3$H-thymidine (15 Ci/mmole) (Schwartz-Mann, Orangeburg, N.Y.). Control wells received DMEM containing either 1% PPP or varying concentrations of human serum 1–10%. The PPP and serum were prepared as described by Clemmons, D. R. (1983) J. Cell Physiol. 114:61–67. The PPP was determined to have approximately 20 pg/ml platelet factor 4 by RIA. Following a 36-hour incubation, the reaction was stopped and the amount of $^3$H-thymidine that had been incorporated into DNA determined by the method of Clemmons, D. R. (1983) J. Cell Physiol. 114:61–67.

Chick embryo fibroblasts were isolated from 14–16 day chicken embryo skin. The primary explants were plated in medium 199 (Gibco) supplemented with 4% FBS (Hyclone), 10% chicken serum, penicillin 100 U/ml and streptomycin 100 ug/ml (Gibco). The cells that grew from the explants were passaged one time then subcultured on 96-well plates (Falcon #3004) at 3,000 cells/well in DMEM supplemented with 10% FBS. After five days the monolayers were washed and test factors added with 0.2 ml DMEM containing 0.5 uCi $^3$H-thymidine and 1% PPP then $^3$H-thymidine incorporation determined after a 36 hour incubation as described previously. Mouse embryo fibroblasts were obtained from 18 day fetal Balb/c mouse (skin) and were grown in DMEM supplemented with 10% FBS, 10 mM glutamine (Sigma, St. Louis, Mo.) and penicillin 100 U/ml streptomycin 100 mcg/ml (Gibco). Cultures between the 3rd and 5th passage were used for all experiments.

Human fibroblasts were purchased from the Human Mutant Genetic Cell Repository (Camden, N.J.). They were maintained in stock cultures in Minimum Essential Medium (MEM) (Gibco) supplemented with 1,000 U/ml penicillin, 100 ug/ml streptomycin and 10% bovine serum (Colorado Serum Co, Denver, Col.). They were passaged every seven days using a passage dilution ratio of 1:4. Cultures between the 4th and 5th passages were plated at a density of 8,000 cells/well on microtest plates for use in individual experiments. After five days the cultures were washed twice with MEM then 0.2 ml MEM containing 1% PPP, 0.5. uCi $^3$H-thymidine and test substances were added then $^3$H-thymidine incorporation determined after 36 hours as described previously.

To determine if the binding protein could potentiate the cell growth response to IGF-I, human fibroblasts or smooth muscle cells were plated at densities of 15,000 cells/cm$^2$ in 24 well plates (Falcon #3003) containing 1.0 cc DMEM plus 10% FBS (smooth muscle) or MEM plus 10% calf serum (fibroblasts). After 2 hours, to allow for cell attachment, the media were aspirated and 1.0 cc of media containing 1% PPP was added. After 12 hours incubation to allow the cells to become quiescent the media were removed and replaced with 1.0 cc of MEM containing 1% PPP and the test substances. After 48 hours of incubation the cultures were exposed to 1.0 cc 0.5% trypsin 0.03% EDTA for 10 min at 37° C. This was removed and added to 9.0 cc of 0.15 mM NaCl and cell number determined using a particle data counter (Coulter, Model ZBI).

The binding protein that had been purified from human amniotic fluid in Example 1 was incubated with quiescent porcine aortic smooth muscle cell cultures. This cell type was chosen because it does not have IGF binding protein that is adherent to its cell surface. Addition of the IGF binding protein alone resulted in minimal stimulation of $^3$H-thymidine incorporation (FIG. 1A). Addition of concentrations of IGF-I (20 ng/ml) or insulin (10 ug/ml) resulted in only 15 and 38% increases in $^3$H-thymidine incorporation respectively. In contrast, addition of IGF-I (20 ng/ml) plus the pure binding protein (100 ng/ml) resulted in 4.4 fold stimulation that exceeded the cellular response to 10% fetal bovine serum. At concentrations of 10 ug/ml, insulin binds to the type I IGF receptor but does not bind to the binding protein. When these concentrations of insulin were added with the binding protein there was no potentiation of the cellular replication response indicating that activation of the binding protein effect was specific for IGF.

To determine if cell types from different species might respond to the IGF binding protein in a similar manner, the effect of this protein plus IGF-I was tested using chick and mouse embryo fibroblast cultures. These cell types were chosen because the chick cells do not synthesize an IGF binding protein but do possess type I IGF receptors. The mouse cells secrete a different form of IGF binding protein (MW est. 22K) and neither cell type has IGF binding protein on their cell surfaces. Addition of pure IGF binding protein resulted in only minimal changes in $^3$H-thymidine incorporation in either cell type, (FIGS. IB and C). In contrast, 100 ng/ml of the binding protein plus IGF-I showed marked potentiation of the cellular response to IGF-I. The chick fibroblasts were particularly sensitive, reaching 81% of the maximal response induced by 10% human serum with only 5 ng/ml IGF-I (FIG. IB). The mouse fibroblasts were also sensitive to the effects of the coincubation of IGF binding protein and IGF-I (FIG. IC). Neither cell type responded to insulin plus IGF binding protein indicating that the binding protein-IGF-I complex had to be formed to achieve the maximal stimulation of $^3$H-thymidine incorporation.

To determine if human fibroblasts, a cell type that synthesizes the IGF binding protein, could also respond to exogenously added peptide, quiescent human fibroblast cultures were prepared as described in FIG. 2. Addition of increasing concentrations of IGF-I resulted in an increase in $^3$H-thymidine uptake into DNA that was maximal at 20 ng/ml and was 82% greater than control cultures that were exposed to 1% PPP alone. The enhanced response to IGF-I alone compared to chick or mouse fibroblasts may have been due to endogenously secreted IGF binding protein. Addition of the IGF binding protein alone resulted in no increase in DNA synthesis. However, when 100 ng/ml of this protein was added with increasing concentrations of IGF-I, DNA synthesis was augmented to a level that was equal to 10% human serum. The inventors have also determined that these cells synthesize and secrete the IGF binding protein into media and that this protein can attach to the cell surface as described in Clemmons, D. R. J. Clin. Invest. 77:1548–1556 (1986). However, fibroblasts only secrete sufficient binding protein to reach media concentrations of 2–5 ng/ml and since 50 ng/ml was added to these cultures this difference probably accounts for the additional increase in $^3$H-thymidine incorporation that was present.

To determine if these responses were dependent upon the concentration of the binding protein, increasing concentrations (1–100 ng/ml) of binding protein plus a constant concentration of IGF-I (10 ng/ml) were incubated with smooth muscle cell cultures. The cultures responded to 2 ng/ml of binding protein with a significant increase in $^3$H-thymidine incorporation but a maximal effect was not obtained until 100 ng/ml was used (FIGS. 2 and 3). Since cultured fibroblasts secrete concentrations of IGF binding protein in the range of 2–5 ng/ml this result indicates that the fibroblasts probably were not secreting a quantity of binding protein sufficient to achieve a maximal DNA synthesis response.

To determine if cells that were stimulated by IGF-I plus the binding protein could traverse the full cell cycle, smooth muscle cells and human fibroblasts were plated at low density and made quiescent by serum deprivation. After 12 hours the binding protein and IGF-I or insulin were added to test cultures and incubated for 60 hours before the cell number was determined. Addition of IGF-I or insulin alone resulted in 3% and 11% increases in smooth muscle cell number, whereas the binding protein plus IGF-I (10 ng/ml) effected a 2.4-fold increase. This increase was greater than that induced by 10% human serum (FIG. 4A). Similar results were obtained with human fibroblasts although the effect of IGF-I alone was greater (FIG. 4B). IGF-I alone resulted in a 31% increase, whereas the combination of binding protein plus IGF-I gave a 2.1-fold increase in cell number after 48 hours.

Example 3

Sequence of IGF-I Binding Protein

1. Two methods have been used to determine amino acid sequences from the stimulatory IGFBP purified from amniotic fluid. The protein was reduced in 0.01 M DTT for one hour at 37° C. and was alkylated with 0.11 M iodoacetic acid. The product was repurified using a reverse phase HPLC column. In method 1, protein from the reverse phase hplc column was concentrated and applied directly to the filter of the Applied Biosystems 470A gas phase sequencer. In method 2, protein was subjected to trypsin digestion (1/50th the amount of protein by weight) for 12 hours in 0.1 M ammonium carbonate pH 8.0. The tryptic peptides were separated by reverse phase hplc on C8 and C4 columns using 0.1% TFA and acetonitrile gradients. After concentration in a Speedvac the peptides were applied to the sequencer and sequenced as per the manufacturers' instructions.

The following sequences have been obtained:
1. APWQCAPCSAEKLAL(E or S) PPVSASESCVTR (this is the N-terminal sequence)
2. WKEPCCIELYR
3. ALPGEQQPLHALTR
4. NGFYHSR
5. FYLPNCNK
6. GQGATVQESDASAP
7. VVESLAK
8. IPGSPEIR
9. ALHVTNIKK To overlap these peptides, and to obtain other peptides, the protein should be digested with other proteases including submaxillary protease (Arg specific), Lys-C protease (Lys specific), and V8-protease (Glu specific) and the peptides fractionated by reverse phase hplc and sequenced as described above.

2. Amino acid sequence from the purified inhibitory IGFBP from the amniotic fluid (see purification in Example 1, above), and the purified stimulatory IGFBP from the GM10 fibroblast (see purification in Example 5, below), and other cell-conditioned media can be obtained in ways analogous to those described above for the stimulatory IGFBP from amniotic fluid.

Example 4

Isolation of the Genes for IGFBPS

Using the antibodies prepared to the amniotic fluid stimulatory IGFBP a variety of cell lines have been identified that make IGFBPs. These cells include lines GM10 and GM498 (Human Mutant Genetic Cell Repository, Camden, N.J.), line MDA 231 (American Type Culture Collection, 12301 Parklawn Dr., Rockville, Md. 20852-1776) and line HEC-1B (A.T.C.C.) To isolate the gene(s) for IGFBPs from these cells they should first be grown to confluence in 10 150 mm plates in the media prescribed by the supplier and RNA should be isolated from these cells using the NP-40 lysis procedure (Maniatis, T., Fritsch, E. F., and Sambrook, J. (1982) *Molecular Cloning. A Laboratory Manual.* Cold Spring Harbor Laboratory, pp. 191–193). PolyA+ RNA can be purified by chromatography on oligo dT cellulose (Aviv, H. and Leder, P. (1972) Proc. Natl. Acad. Sci. (USA) 69, 1408–1412). Five ug of this RNA should be used to synthesize blunt-ended double-stranded cDNA using the method described by Gubler and Hoffman (Gubler, U. and Hoffman, B. J. (1983) Gene 25, 263–269). EcoRI linkers should be attached, and the resulting cDNA cloned into lamda gt11 (Young, R. A. and Davis, R. W. (1983) Proc. Natl. Acad. Sci. (USA) 80, 1194–1198).

The resulting library, which should contain upwards of $10^6$ independent clones, may be screened on *E. coli* Y1090 with an appropriate polyclonal rabbit antibody to stimulatory IGFBP from amniotic fluid purified as described in Example 1, using screening conditions described by Young and Davis. Positive signals will be detected using an alkaline phosphatase conjugated 2nd antibody (goat anti-rabbit ProMega Biotec) as described by the manufacturer. Clones testing positive to this antibody should then be probed with three mixed sequence oligonucleotide probes based on IGFBP amino acid sequence (described previously). Probe #1, a 23 mer, is a mixture of 192 sequences consisting of all possible DNA sequences for the amino acid sequence W K E P C C I E. Probe #2, a 17 mer, is a mixture of 64 sequences consisting of all possible DNA sequences for the amino acid sequence W Q C A P C. Probe #3, a 17 mer, is a mixture of 64 sequences consisting of all possible DNA sequences for the amino acid sequence P G E Q Q P. These probes can be synthesized on an Applied Biosystems DNA synthesizer and should be 5' end labeled to a specific activity of 4–6×$10^6$ cpm/pmol using [gamma-32P]-ATP and T4 polynucleotide kinase. The clones testing positive to the antibody should be plated on *E. coli* Y1088 and the DNA transferred to nitrocellulose as described (Benton, W. D. and Davis, R. W. (1977) Science 196, 180–182).

The probing should be done in a hybridization buffer containing 1.0M NaCl, 0.1M Sodium Citrate, 2× Denhardts solution (Denhardt, D. T. (1966) Biochem. Biophys. Res. Commun. 23, 641–646), 0.1% SDS, 0.05% Sodium Pyrophosphate, and 150 mg/ml yeast tRNA. The filters should be hybridized for 12–16 hrs, using 0.4 pmol/ml of oligonucleotide, at a temperature 2° C. below the calculated Tm for the most AT-rich member of each pool of oligonucleotides (Suggs, S. V. (1981) In Brown, D. D. and Fox, C. F. (eds). Developmental Biology Using Purified Genes, Academic Press, New York, pp. 683–693.) These temperatures are as follows: Probe #1, 60° C.; Probe #2, 50° C.; Probe #3, 50° C. After hybridization, filters should be washed for 45 minutes at ambient temperature with three changes of 1M NaCl, 0.1M, Sodium Citrate, and 0.1% SDS. A stringent wash of five minutes should be done at the calculated Tm (i.e. 2° C. above hybridization temp.) for the most AT rich member of each pool of probes. Filters should be dried and positive signals detected by autoradiography. Clones testing positive to the antibody and both probes should be subcloned into the M13 sequencing vectors mp 18 and mp 19 (Yanisch-Perron, C., Vieira, J., and Messing, J. (1985) Gene 33, 103–119 and sequenced as described (Sanger, F. and Coulson, A. R. (1975) J. Mol. Biol. 94, 441–448).

In the event that no antibody positive clones are obtained in the first part of the library screening the entire library should be subjected to the oligonucleotide screening procedure described above. In addition to the oligonucleotides described, further oligonucleotides should be used as indicated by protein sequence determined on the purified proteins (see Examples 1 and 5). The design and synthesis of these oligonucleotide probes is known to one skilled in the art.

In addition to cell lines, natural human tissues should be considered as sources of RNA with which to make a cDNA library. A suitable source of tissue is the decidua of the uterus.

A full length clone will be characterized by its containing an open reading frame coding for protein sequences known to be present in IGFBP and start and stop codons. If no full length clone is isolated one can be assembled from a complete set of partial clones and suitable synthetic DNAs by methods familiar to one versed in the art. The insert from a full length clone should be transferred into an expression vector as described in Example 6.

Example 5

Purification of Fibroblast IGFBP

Conditioned media from human skin fibroblast cell lines GM10 or GM498 (Human Mutant Genetic Cell Repository, Camden, N.J.) is centrifuged at 20,000×g for 20 minutes to remove debris. Ammonium sulfate is added to the supernatant to a final concentration of 65% and the solution allowed to stir slowly at 4° C. for 30 min. The pellet from a 20,000×g centrifugation for 30 min. is extracted with 10 mM ammonium carbonate pH 7.2 containing 0.5 M NaCl. The extracts are fractionated by chromatography on Sephadex G-100 equilibrated in the extraction buffer. Fractions containing IGF-1 binding activity are pooled and reprecipitated with 65% ammonium sulfate.

The pellet from a 20,000×g centrifugation for 30 min. is extracted with 10 mM ammonium carbonate pH 6.5 and diluted with distilled water to a conductivity equal to that of 50 mM NaCl. The solution is applied at a rate of 15 ml/hour to a heparin sepharose column previously equilibrated with 10 mM ammonium carbonate pH 6.5 and 50 mM NaCl. The column is washed with three volumes of the equilibration buffer containing 1 M NaCl and then three volumes of buffer containing 2 M NaCl. The column containing buffer with 2 M NaCl is allowed to stand at 4° C. overnight and in the morning is eluted once more with one volume of 2 M NaCl. The pooled 2 M NaCl washes are pooled and reverse dialysed against 10 mM ammonium carbonate pH 6.5 and 50 mM NaCl.

The dialysate is applied at 15 ml/hour to an IGF-1 affinity column, prepared from 2 mg of IGF-1 and 3 ml of Reactigel X (Pierce Chemical) according to the manufacturers' instructions, which was preequilibrated with 10 mM ammonium carbonate pH 6.5 50 mM NaCl. The column is washed with five volumes of equilibration buffer and then with five volumes of 10 mM ammonium acetate pH 4.5 50 mM NaCl. The IGFBP activity is then eluted with 1 M acetic acid.

The active fractions are applied to a Vydac C-4 reverse phase hplc column and eluted with 0.04% aqueous TFA for 5 min at 1 ml/min followed by a linear gradient of acetonitrile to 25% over a period of 3 min. The protein is then eluted with a linear gradient of from 25% to 100% acetonitrile over a period of 30 min, eluting close to 30% acetonitrile. If insufficiently pure for sequencing at this stage the protein is diluted in water and reapplied to a Vydac C-8 column. It is eluted with the same gradient applied to the C-4 column, eluting at about 50% acetonitrile.

Example 6

Expression of Genes for IGFBP in Animal Cells

To express IGFBP in animal cells the following steps should be carried out:
1. Construction of an expression vector
2. Choice of a host cell line
3. Introduction of the expression vector into the cells
4. Induction of expression of IGFBP.

1. To construct an IGFBP expression vector that will function in many different cell types a plasmid should be constructed as follows. pBR322 should be digested with EcoR1 and EcoRV and the EcoR1 sticky end should be blunt-ended by treatment with Klenow DNA polymerase in the presence of dATP, and dTTP. The large fragment should be isolated and ligated to the 4 Kb EcoRI fragment of pMK. (Brinster et al. Cell 27 223–231, 1981) carrying the MT1 promoter and the structural gene for herpes simplex type 1 thymidine kinase (HSV-1 tk), blunt ended as described above. The ligation mixture should be transformed into E.coli JM109 and plasmid DNA prepared from ampicillin resistant, tetracycline sensitive transformants. The DNA should be characterized by restriction mapping and a plasmid conforming to the structure drawn in FIG. 5 selected for further work.

The Bgl II site of this plasmid should be converted to an EcoR1 site by digesting the DNA with Bgl II and cloning into the linearised DNA a suitable piece of synthetic DNA containing an EcoR1 site using standard methods. The resulting plasmid, pMK-SGE, should be amplified in E.coli, reisolated by standard methods, and linearised with EcoR1.

Full length IGFBP cDNA isolated from the DNA of lambda gt11 clones by standard methods that include digestion of the DNA with EcoR1 and gel purification should be ligated into the EcoRI site of the MT-1 promoter plasmid pMK-SGE described above. Following this ligation and transformation of E coli, a clone should be selected in which the IGFBP CDNA is in the same orientation as the MT-1 promoter as determined by restriction mapping. Plasmid DNA should be prepared for transformation of animal cells.

2. Because the active IGFBPs may have as yet uncharacterized postranslational modifications the genes should be expressed in cells as like as possible to their natural cell of origin. The procedure to be followed is illustrated here using the gene for the stimulatory IGFBP from fibroblasts. Similar procedures should be followed with genes for the other proteins once suitable producer cell lines have been identified. Until that time fibroblasts will act as producer cells for those IGFBPs as well.

3. To introduce the expression vector into Ltk$^-$ cells or other TK$^-$ fibroblast lines, the expression vector should be mixed with pHSV-106 plasmid DNA (Bethesda Research Labs) which carries the HSV-1 TK gene. The mixed DNAs should be applied to the cells using the standard calcium phosphate-DNA precipitation techniques S. L. Graham and A. J. Von der Eb (1973) Virology Vol. 52:456–467. Stable transformants can be selected by their ability to grow in medium containing hypoxanthine, aminopterin and thymidine M. Wigler et al. (1979) Cell 16:777–785.

To introduce the IGFBP expression vector DNA into fibroblasts that are not Tk$^-$ it should be mixed with a selection vector prepared by fusing the SV40 promoter in pKSV-10 with the neomycin resistance (aminoglycoside 3'-phosphotransferase) gene (Pharmacia) and cotransformed into the cells as described above. Stable transformants can be selected by their ability to grow in the presence of the antibiotic G418.

A third method for introducing the expression vector into mammalian cells is to cotransform the expression vector with a plasmid carrying a functional dihydrofolate reductase (DHFR) gene. Stable transformants can be selected by growing the cells in methotrexate. This method is particularly suitable for stable transfaction of DHFR$^-$ CHO cells F. McCormick et al. (1984) Mol. Cell. Biol. 4:166–172.

To induce expression of the IGFBP genes in each of the above stably transformed animal cells, the cells should be exposed to 10 mM cadmium sulfate in the growth medium. The MT-1 promoter is induced by this treatment and should result in an increase in expression of the IGFBP gene of approximately 7 fold. (Mayo, K. E., R. Warren and R. D. Palmiter 1982 Cell 29:99–108).

To increase expression of the IGFBP further the copy number of the IGF-1 stimulator DNA should be amplified by one of the following methods. In the case where the expression vector was cotransformed with the TK gene, amplification should be brought about by decreasing the thymidine concentration in the medium or omitting it entirely. In the case in which the expression vector was introduced into cells by cotransformation with the DHFR gene, amplification of the gene should be brought about by increasing concentration of methotrexate in the medium. (F. McCormick et al. (1984) Mol. Cell. Biol 4:166–172)

Example 7

Purification of IGFBPS From Recombinant Animal Cells

Since the IGFBPs are expected to be secreted from cells like the natural material it is anticipated that the methods described above for purification of the natural protein will allow similar purification and characterization of the recombinant protein.

Example 8

A lambda gt-11 human uterus decidua cDNA library was created as described previously and screened with a rabbit polyclonal antibody to stimulatory insulin-like growth factor binding protein (IGFBP) by the method of Young and Davis as described in Example 4. The rabbit polyclonal antibody was that described in Example 1. Positive signals were detected using an alkaline phosphate conjugated second antibody (goat-anti-rabbit, Pro Mega Biotec) as described by the manufacturer. Approximately 0.12% of the clones in the library tested positive to the antibody. Twelve independent clones were purified and the inserts compared by agarose gel electrophoresis. A clone with an insert of approximately 1500 BP was subcloned into the M13 sequencing vector mp 18 in both orientations and the sequence was determined by the method of Sanger et al. This clone contained a single open reading frame of 776 BP encoding a 24 amino acid signal sequence followed by a 233 amino acid polypeptide that included all peptide sequences previously described.

The sequence has been determined and is set forth in FIG. 6.

This sequence contains a tripeptide ArgGlyAsp. This tripeptide or peptides which contain this tripeptide and flanking residues from the IGFBP sequence may serve to prevent cell or matrix attachment of IGFBP and thereby prevent its stimulatory effect on IGF-1 induced cell growth.

Example 9

Figure 7:
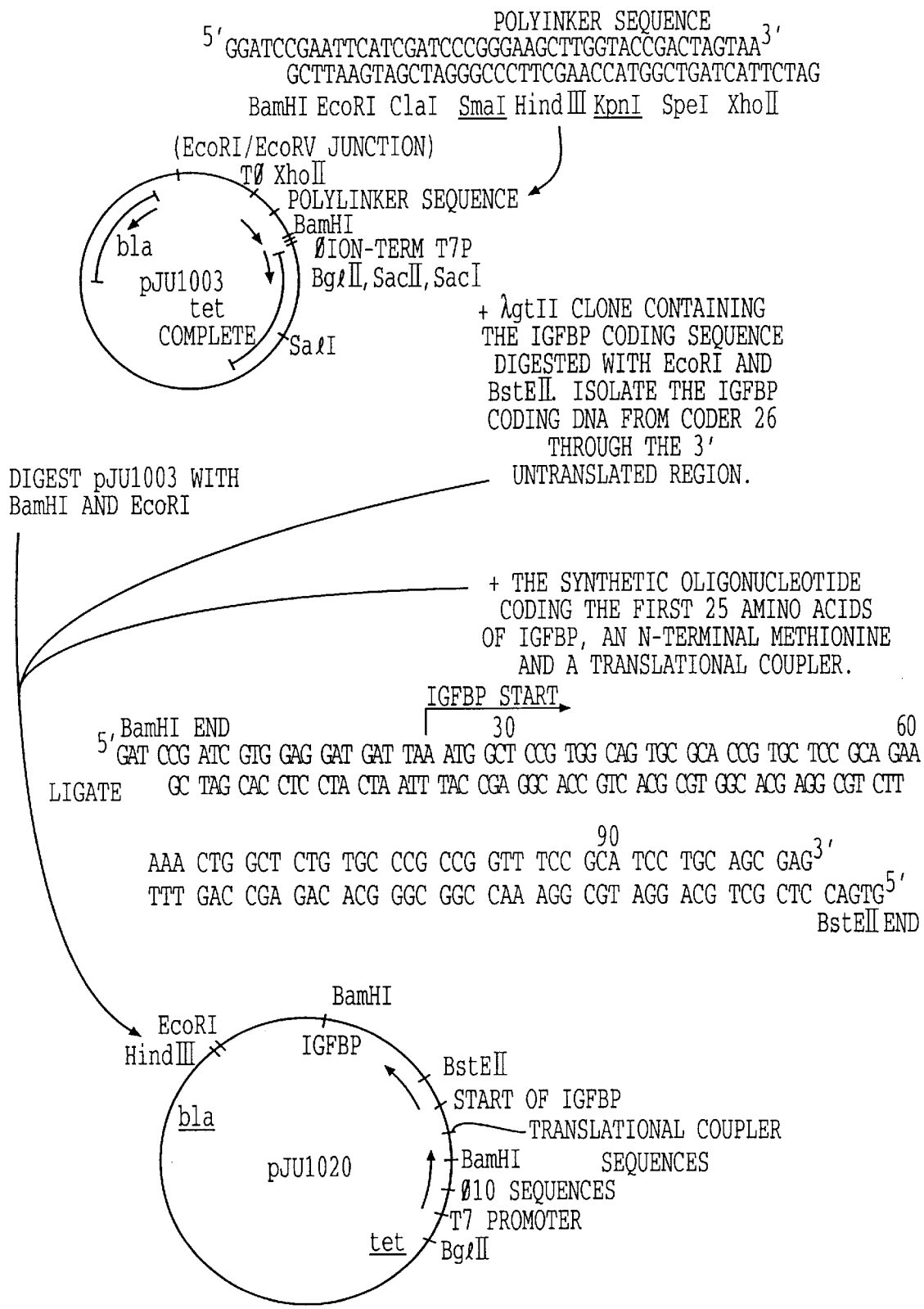
FIG. 7 depicts the creation of plasmid pJU1020 containing the IGFBP coding sequence.

Expression of the IGFBP Gene in Procaryotic (*E. coli*) Cells and the Isolation of Biologically Active IGFBP From Them A. Preparation of Expression Vectors for IGFBP The IGFBP cDNA has been cloned into the *E. coli*, T7 RNA polymerase-dependent expression vector pJU1003 by the following steps as illustrated in FIG. 7.

1. Plasmid pJU1003 was digested with the restriction enzymes BamHI and EcoRI and the large linear vector fragment purified by standard gel methods.

2. The lambda gt11 clone containing the IGFBP cDNA coding sequence was digested with the enzymes EcoRI and BstE11, releasing a fragment of 1225 bp that contains the mature IGFBP coding sequence from codon 26 through the C-terminus and an additional 600 bp of 3' untranslated sequence. This fragment was also purified by standard gel methods.

3. The synthetic double-stranded oligonucleotide of 102 bp shown in FIG. 7 coding for the first 25 amino acids of IGFBP and an N-terminal methionine (ATG) codon was prepared. The codons chosen reflect *E. coli's* preference for certain codons in highly expressed genes. In addition, the 5' end of this oligonucleotide contains DNA sequences that result in translational coupling of the vector-encoded T7 010 gene as described by Rosenberg, A. H., Lade, B. N., Chui, D., Lin, S., Dunn, J. J., Studier, F. W., in Gene 56:125–135, 1987, specifically incorporated herein by reference, to the IGFBP gene. The oligonucleotide has BamHI and BstE11 cohesive ends.

4. The three DNA sequences described above were ligated together, and that mixture was used to transform *E. coli* strain BL21/DE3 described by Studier, F. W., and Moffatt, B., in J. Mol. Biol. 189:113–130, 1986, specifically incorporated herein by reference. Colonies resistant to 15 ug/ml tetracycline were selected and screened for production of IGFBP following induction with 1 mM isopropyl B-D-thiogalactopyranoside (IPTG) using the anti-IGFBP antibody as described in Example 4 above.

5. Plasmid DNA was prepared from a positive clone, and that part resulting from the synthetic oligonucleotide was sequenced according to the method of Sanger and Coulson described in J. Mol. Biol. 94:441–448, 1975, specifically incorporated herein by reference.

A transformant called pJU1020 was isolated as described above and was grown up in liquid media. The amount of IGFBP produced following induction with 1 mM IPTG was estimated by SDS PAGE of total cellular protein using purified native (amniotic fluid) IFGBP as the standard. It was estimated that approximately 1 ug of IGFBP/ml of culture/ $A_{600}$ unit was produced. Importantly, this material migrated in the gel with the same apparent molecular weight as the native protein, 31 kD. This observation shows by this criterion that material identical to the native IGFBP can be produced in *E. coli*.

Figure 8:
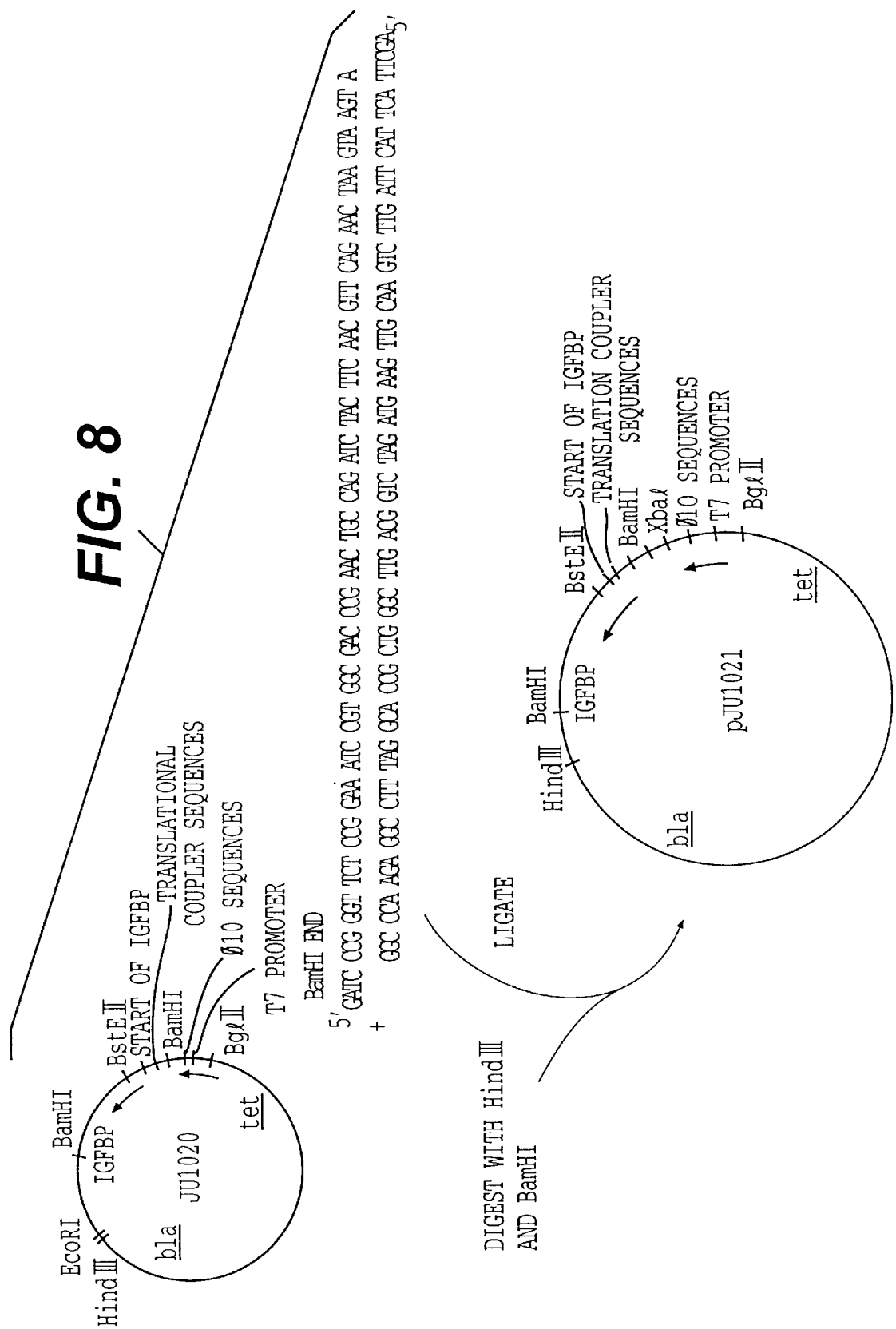
FIG. 8 depicts the creation of plasmid pJU1021 containing the IGFBP coding sequence.

To make a more efficient producer of IGFBP, the 3' untranslated portion of the cDNA clone was removed from plasmid pJU1020 in the following way as shown in FIG. 8.

1. The plasmid was digested with the restriction enzymes BamHI and HindIII.

2. The synthetic double-stranded oligonucleotide of 74 bp shown in FIG. 8 was prepared. This oligonucleotide comprises (a) the coding sequence for the C-terminal 21 codons of IGFBP using codons favored by *E. coli*; (b) a translation termination codon for IGFBP; (c) additional translation termination codons in the other translation reading frames; (d) terminal HindIII and BamHI restriction sites.

3. The synthetic oligonucleotide is then mixed with the digested DNA described in (1) and ligated together. After ligation, the mixture was digested with the enzyme EcoRI. This procedure linearizes only those molecules containing the 3' untranslated DNA since this site is unique to that DNA in this experiment.

4. This mixture was then used to transform *E. coli* strain BL21/DE3 with selection for tetracycline-resistant (15 ug/ml) clones. Transformants were screened for IGFBP production and correctness of the DNA sequence of the synthetic oligonucleotide portion of the clone as described in connection with the pJU1020 construction above.

A positive and correct clone (pJU1021) was grown and the production of IGFBP following induction of gene expression measured as described with the pJU1021 construction described above. This clone produces approximate 20 ug of IGFBP/ul of culture/$A_{600}$ unit.

Figure 9:
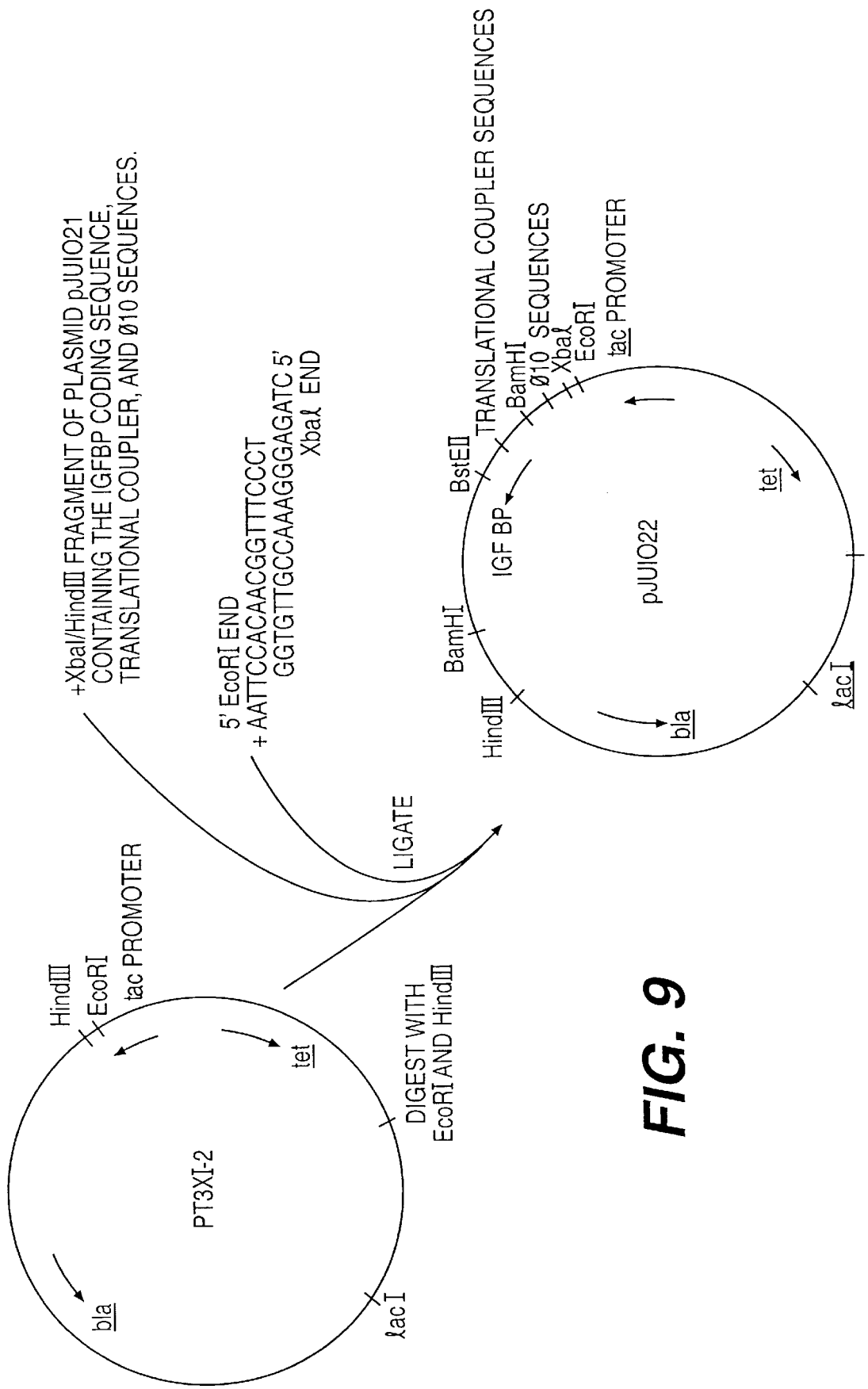
FIG. 9 depicts the creation of plasmid pJU1022 containing the IGFBP coding sequence.

The T7 gene 10 coupled IGFBP sequence described above was transferred to a plasmid vector containing the tacI promoter as described by deBoer, H. A., Comstock, L. J. and Vassar, M., in Proc. Natl. Acad. Sci. USA 8021–25, 1983, specifically incorporated herein by reference, by the following steps as set forth in FIG. 9.

1. Plasmid pT3XI-2, an *E. coli* expression plasmid containing the tac promoter, was digested with the enzymes EcoRI and HindIII and the large fragment containing the promoter, antibiotic resistance genes and origin of replication was isolated.

2. Plasmid pJU1021 was digested with the enzymes XbaI and HindIII and the fragment containing the IGFBP coding sequence isolated. This fragment also contains the T7 gene 10 sequences and the translational coupler as described in connection with the pJU1021 construction described above.

3. A synthetic oligonucleotide 20 bp in length was prepared. This fragment contains the DNA sequence just upstream (5') to the XbaI site of plasmid pJU1021. This DNA is used to adapt the IGFBP coding sequence to the tac promoter containing expression plasmid.

4. These three DNA sequences were ligated together and the mixture used to transform *E. coli* strain JM107 with tetracycline-resistant clones selected. Clones expressing IGFBP following gene induction with 1 mM IPTG and containing the correct DNA sequence of the synthetic oligonucleotide were identified as described above. A positive and correct clone was called pJU1022. This clone was grown and the production of IGFBP following induction of gene expression was measured as described with the pJU1020 construction. This clone produces approximately 10 ug of IGFBP/ml of culture /$A_{600}$ unit.

B. Production of IGFBP from *E. coli*

Preparation of biologically active IGFBP from *E. coli* was done in the following way. *E. coli* strain BL21/DE3 containing plasmid pJU1021 was grown at 37° C. in Luria broth containing 15 ug/ml of tetracycline to an $A_{600}$ of 1.0. One mM IPTG was then added to induce IGFBP gene expression, and the growth continued for 2 hours. Then the cells were harvested by centrifugation and resuspended in one-twentieth their original culture volume in 50 mM Tris, pH 7.5, and lysed in a French pressure cell. Following centrifugation at 15,000×g for 10 minutes, the pellet (insoluble protein) and supernatant (soluble protein) were analyzed by SDS-PAGE for the presence of IGFBP, Western blotting using rabbit anti-IGFBP antibodies. Approximately 80% of the total IGFBP was found in the insoluble fraction.

Biologically active IGFBP has been obtained from this function by three different methods.

1. The pellet can be washed with 50 mM Tris, pH 7.5 (1/20 original culture volume. Approximately 5% of the IGFBP will then solubilize and remain in the supernatant following centrifugation. This material contains monomeric, dimeric and higher molecular weight variants of IGFBP and has been shown to potentiate the activity of IGF-1 in the porcine aortic smooth muscle cell bioassay described above.

2. The insoluble protein pellet prepared as described above can be resuspended in 6 M Guanidine HCL (1 ml/50 ml of original cell culture), and left at room temperature for 5 minutes. Dithiothreitol is added to a final concentration of 20 mM, and the mixture left at room temperature for 30 minutes. This mixture is centrifuged at 13,000×g for 15 minutes and the supernatant is mixed with oxidized glutathione to a final concentration of 20 mM and the mixture left at room temperature for 10 minutes.

4.5 ml of 50 mM tris pH 10.7 per 50 ml of original culture and cysteine to 1 mM final contration are added to the mixture and it is left at room temperature overnight. The mixture is then dialyzed against 50 mM tris pH 7.5 and centrifuged at 13,000×g for 15 minutes to remove the insoluble materia.

The IGFBP obtained from this procedure is called "refolded IGFBP". When it is analyzed by SDS-PAGE without prior reduction, it can be shown to contain a dimetric form of IGFBP (apparent molecular weight 50 kDa) as well as the monomeric form (apparent molecular weight 25 kDa). Both of these forms bind IGF-1 as shown by an in vitro assay showing the binding of $^{125}$I-labelled IGF-1 to IGFBP transferred to a nitro-cellulose filter following non-reducing SDS-PAGE. The refolded material potentiates the activity of IGF-1 in the mitogenicity assay using porcine aortic smooth muscle cells as described.

Monomeric IFGBP can be purified free of dimeric by FPLC (Mono Q) with the monomers eluting at 0.28 M NaCl. This fraction containing only monomers does not potentiate the activity of IGF-1 in the mitogenicity assay using porcine aortic smooth muscle cells as described.

3. The insoluble protein pellet can be solubilized with 6 M guanidine hydrochloride as above but without the addition of dithiothreitol and centrifuged. If this material is then dialyzed against 50 mM tris pH 7.5, a precipitate forms. However, if this precipitate and the soluble protein are compared by SDS-PAGE, it is found that at least 50% of the IGFBP solubilized by 6 M Guanidine HCL remains in solution following dialysis. This solubilized material can be shown to contain monomeric and dimeric forms of IGFBP that bind IGF-1 as described above. This guanidine solubilized and dialyzed IGFBP has also been shown to potentiate the activity of IGF-1 in the mitogenicity assay using porcine aortic smooth muscle cells as described.

It will be apparent to those skilled in the art that various modifications and variations can be made in the processes and products of the present invention. Thus, it is intended that the present invention cover the modifications and variations of this invention provided they come within the scope of the appended claims and their equivalents.

What is claimed is:

1. An isolated recombinant insulin-like growth factor binding protein that potentiates the activity of insulin-like growth factor, said insulin-like growth factor binding protein being produced by a host cell containing a recombinant DNA molecule selected from the group consisting of (1) a DNA molecule encoding insulin-like growth factor binding protein having the amino acid sequence set forth in FIG. 6, and (2) a DNA molecule encoding an amino acid sequence that is at least 80% identical to the amino acid sequence set forth in FIG. 6.

2. An insulin like growth factor binding protein according to claim 1, wherein the host cell is *E. coli*.

* * * * *